(12) United States Patent
Dekker et al.

(10) Patent No.: US 9,273,309 B2
(45) Date of Patent: Mar. 1, 2016

(54) MAPPING OF GENOMIC INTERACTIONS

(75) Inventors: Job Dekker, Princeton, MA (US); Josee Dostie, Montreal (CA)

(73) Assignee: University of Massachusetts, Boston, MA (US)

( * ) Notice: Subject to any disclaimer, the term of this patent is extended or adjusted under 35 U.S.C. 154(b) by 1625 days.

(21) Appl. No.: 12/310,427

(22) PCT Filed: Aug. 24, 2007

(86) PCT No.: PCT/US2007/018745
§ 371 (c)(1),
(2), (4) Date: Feb. 9, 2010

(87) PCT Pub. No.: WO2008/024473
PCT Pub. Date: Feb. 28, 2008

(65) Prior Publication Data
US 2010/0130373 A1    May 27, 2010

Related U.S. Application Data

(60) Provisional application No. 60/839,748, filed on Aug. 24, 2006.

(51) Int. Cl.
*C12N 15/10*    (2006.01)

(52) U.S. Cl.
CPC ........ *C12N 15/1072* (2013.01); *C12N 15/1093* (2013.01)

(58) Field of Classification Search
None
See application file for complete search history.

(56) References Cited

PUBLICATIONS

Barany (1991 PNAS 88:189-193).*
Dekker et al (2002 Science 295:1306-1311).*
Rimsky et al (2004 Current Opinion in Microbiology 7: 109-114).*
Fan et al (2004 Genome Research 14: 878-85).*
Marguilies et al (2005 Nature 437:376-80).*
Fangman et al (1991 Annu. Rev. Cell Biol. 7:375-402).*
Dostie et al (2006 Genomic Research 16:1299-1309).*
Bibikova, M. et al. (2006) "High-throughput DNA methylation profiling using universal bead arrays," *Genome Res.* 16(3), 383-393.
Bulger, M. et al. (2003) "A Complex Chromatin Landscape Revealed by Patterns of Nuclease Sensitivity and Histone Modification within the Mouse β-Globin Locus," *Mol. Cell. Biol.* 23(15), 5234-5244.
Calzolari, R. et al. (1999) "Deletion of a region that is a candidate for the difference between the deletion forms of hereditary persistence of fetal hemoglobin and [delta][beta]-thalassemia affects [beta]- but not [gamma]-globin gene expression," *EMBO J.* 18(4), 949-958.
Carter, D. et al. (2002) "Long-range chromatin regulatory interactions in vivo," *Nat. Genet.* 32(4), 623-626.
Chakalova, L. et al. (2005) "The Corfu δβ thalassemia deletion disrupts γ-globin gene silencing and reveals post-transcriptional regulation of HbF expression," *Blood* 105(5), 2154-2160.
Chambeyron, S. et al. (2004) "Does looping and clustering in the nucleus regulate gene expression?," *Curr. Opin. Cell Biol.* 16(3), 256-262.
de Laat, W. et al. (2003) "Spatial organization of gene expression: the active chromatin hub," *Chromosome Res.* 11(5), 447-459.
Dekker, J. (2003) "A closer look at long-range chromosomal interactions," *Trends Biochem. Sci.* 28(6), 277-280.
Dekker, J. (2006) "The three 'C' s of chromosome conformation capture: controls, controls, controls," *Nat. Meth.* 3(1), 17-21.
Dekker, J. et al. (2002) "Capturing Chromosome Conformation," *Science* 295(5558), 1306-1311.
Doty, P. et al. (1960) "Strand Separation and Specific Recombination in Deoxyribonucleic Acids: Physical Chemical Studies," *P.N.A.S.* 46(4), 461-476.
Drissen, R. et al. (2004) "The active spatial organization of the β-globin locus requires the transcription factor EKLF," *Genes Dev.* 18(20), 2485-2490.
Fan, J.-B. et al. (2004) "A Versatile Assay for High-Throughput Gene Expression Profiling on Universal Array Matrices," *Genome Res.* 14(5), 878-885.
Farrell, C. M. et al. (2002) "Conserved CTCF Insulator Elements Flank the Mouse and Human β-Globin Loci," *Mol. Cell. Biol.* 22(11), 3820-3831.
Fraser, P. et al. (1993) "Each hypersensitive site of the human beta-globin locus control region confers a different developmental pattern of expression on the globin genes," *Genes Dev.* 7(1), 106-113.
Gheldof, N. et al. (2006) "The active FMR1 promoter is associated with a large domain of altered chromatin conformation with embedded local histone modifications," *P.N.A.S.* 103(33), 12463-12468.
Gombert, W. M. et al. (2003) "The c-myc Insulator Element and Matrix Attachment Regions Define the c-myc Chromosomal Domain," *Mol. Cell. Biol.* 23(24), 9338-9348.
Gribnau, J. et al. (2000) "Intergenic Transcription and Developmental Remodeling of Chromatin Subdomains in the Human β-globin Locus," *Mol. Cell* 5(2), 377-386.
Hardenbol, P. et al. (2005) "Highly multiplexed molecular inversion probe genotyping: Over 10,000 targeted SNPs genotyped in a single tube assay," *Genome Res.* 15(2), 269-275.
Kim, T. H. et al. (2005) "A high-resolution map of active promoters in the human genome," *Nature* 436(7052), 876-880.
Landegren, U. et al. (1988) "A ligase-mediated gene detection technique," *Science* 241(4869), 1077-1080.

(Continued)

*Primary Examiner* — Christopher M Gross

(74) *Attorney, Agent, or Firm* — Medlen & Carroll, LLP

(57) ABSTRACT

The present invention relates to genomic analysis. In particular, the present invention provides methods and compositions for mapping genomic interactions.

34 Claims, 17 Drawing Sheets

(56) References Cited

PUBLICATIONS

Li, J. et al. (2005) "A colorimetric method for point mutation detection using high-fidelity DNA ligase," *Nucleic Acids Res.* 33(19), e168.

Li, Q. et al. (2002) "Locus control regions," *Blood* 100(9), 3077-3086.

Ling, J. Q. et al. (2006) "CTCF Mediates Interchromosomal Colocalization Between Igf2/H19 and Wsb1/Nf1," *Science* 312(5771), 269-272.

Liu, Z. et al. (2005) "Long-Range Interactions between Three Transcriptional Enhancers, Active Vκ Gene Promoters, and a 3' Boundary Sequence Spanning 46 Kilobases," *Mol. Cell. Biol.* 25(8), 3220-3231.

Margulies, M. et al. (2005) "Genome sequencing in microfabricated high-density picolitre reactors," *Nature* 437(7057), 376-380.

Marmur, J. et al. (1960) "Strand Separation and Specific Recombination in Deoxyribonucleic Acids: Biological Studies," *Proceedings of the National Academy of Science of the United States of America* 46(4), 453-461.

Murrell, A. et al. (2004) "Interaction between differentially methylated regions partitions the imprinted genes Igf2 and H19 into parent-specific chromatin loops," *Nat. Genet.* 36(8), 889-893.

Nuwaysir, E. F. et al. (2002) "Gene Expression Analysis Using Oligonucleotide Arrays Produced by Maskless Photolithography," *Genome Res.* 12(11), 1749-1755.

O'Neill, D. et al. (1999) "Tissue-specific and developmental stage-specific DNA binding by a mammalian SWI/SNF complex associated with human fetal-to-adult globin gene switching," *P.N.A.S.* 96(2), 349-354.

Palstra, R.-J. et al. (2003) "The [beta]-globin nuclear compartment in development and erythroid differentiation," *Nat. Genet.* 35(2), 190-194.

Patrinos, G. P. et al. (2004) "Multiple interactions between regulatory regions are required to stabilize an active chromatin hub," *Genes Dev.* 18(12), 1495-1509.

Peterson, K. R. et al. (1996) "Effect of deletion of 5'HS3 or 5'HS2 of the human beta-globin locus control region on the developmental regulation of globin gene expression in beta-globin locus yeast artificial chromosome transgenic mice," *P.N.A.S.* 93(13), 6605-6609.

Rippe, K. (2001) "Making contacts on a nucleic acid polymer," *Trends Biochem. Sci.* 26(12), 733-740.

Selzer, R. R. et al. (2005) "Analysis of chromosome breakpoints in neuroblastoma at sub-kilobase resolution using fine-tiling oligonucleotide array CGH," *Genes, Chromosomes and Cancer* 44(3), 305-319.

Singh-Gasson, S. et al. (1999) "Maskless fabrication of light-directed oligonucleotide microarrays using a digital micromirror array," *Nat. Biotechnol.* 17(10), 974-978.

Spilianakis, C. G. et al. (2004) "Long-range intrachromosomal interactions in the T helper type 2 cytokine locus," *Nat. Immunol.* 5(10), 1017-1027.

Spilianakis, C. G. et al. (2005) "Interchromosomal associations between alternatively expressed loci," *Nature* 435(7042), 637-645.

Splinter, E. et al. (2003) "3C Technology: Analyzing the Spatial Organization of Genomic Loci In Vivo," in *Methods in Enzymology* (Allis, C. D., et al., Eds.), pp. 493-507, Academic Press.

Stamatoyannopoulos, G. (2005) "Control of globin gene expression during development and erythroid differentiation," *Exp. Hematol.* 33(3), 259-271.

Tolhuis, B. et al. (2002) "Looping and Interaction between Hypersensitive Sites in the Active β-globin Locus," *Mol. Cell* 10(6), 1453-1465.

Vakoc, C. R. et al. (2005) "Proximity among Distant Regulatory Elements at the β-Globin Locus Requires GATA-1 and FOG-1," *Mol. Cell* 17(3), 453-462.

Wang, Y. et al. (2005) "Allele quantification using molecular inversion probes (MIP)," *Nucleic Acids Res.* 33(21), e183.

West, A. G. et al. (2005) "Remote control of gene transcription," *Hum. Mol. Genet.* 14(suppl 1), R101-R111.

Xu, N. et al. (2006) "Transient Homologous Chromosome Pairing Marks the Onset of X Inactivation," *Science* 311(5764), 1149-1152.

Yuen, T. et al. (2002) "Accuracy and calibration of commercial oligonucleotide and custom cDNA microarrays," *Nucleic Acids Res.* 30(10), e48.

\* cited by examiner

Figure 12
Table 3.

Figure 13
Table 5.

Figure 14
Table 6

Figure 15
Table 7

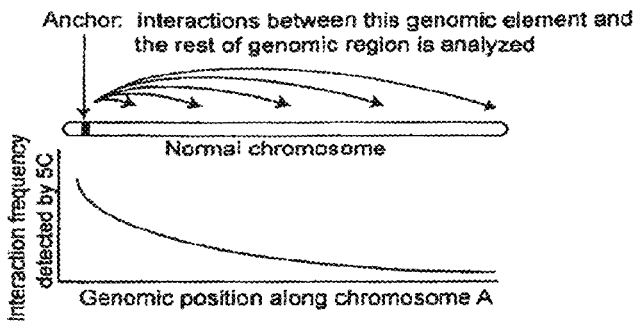
Figure 16
Inversions and duplications
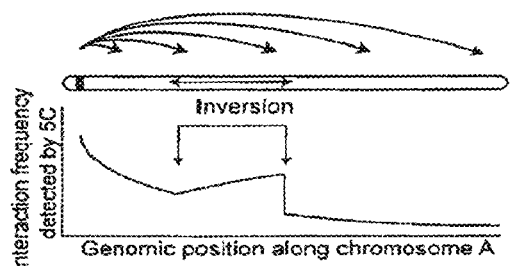
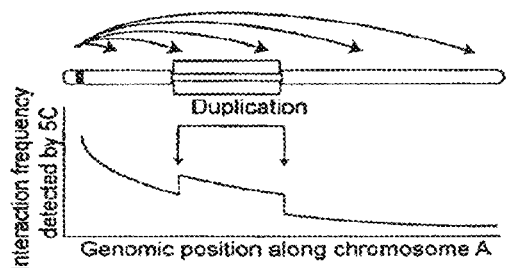
Deletions
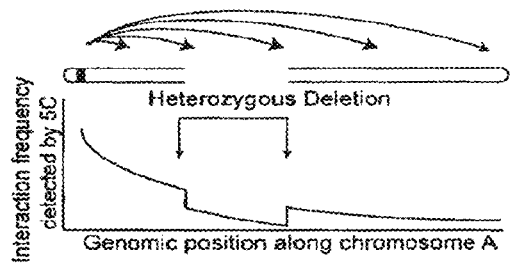
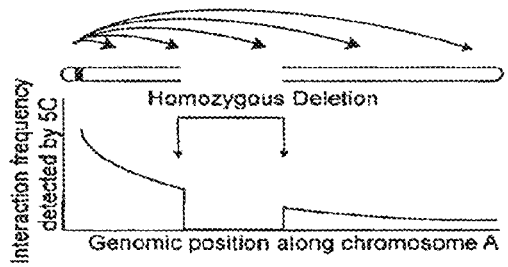
Translocations
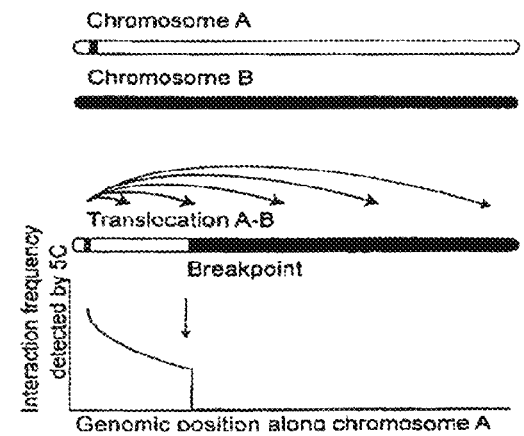
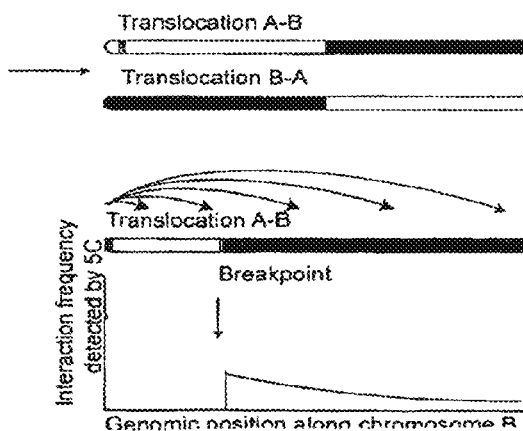

Figure 17 Absence of diagnostic signature interactions
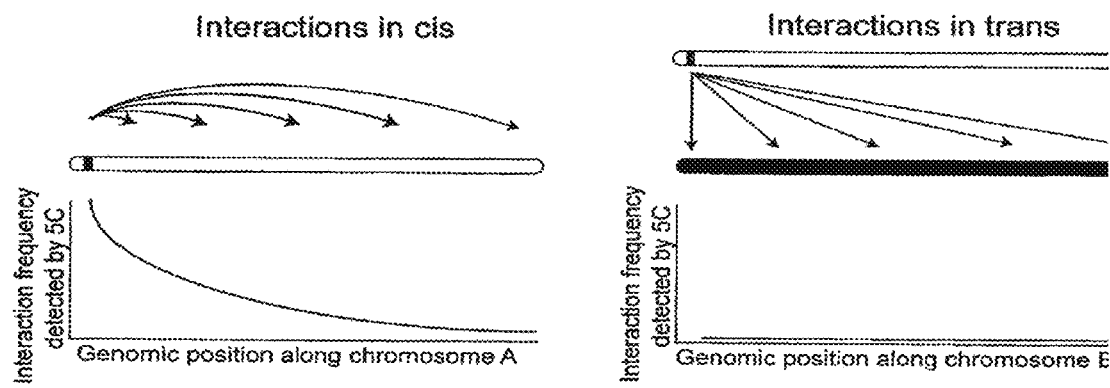
Presence of diagnostic signature interactions
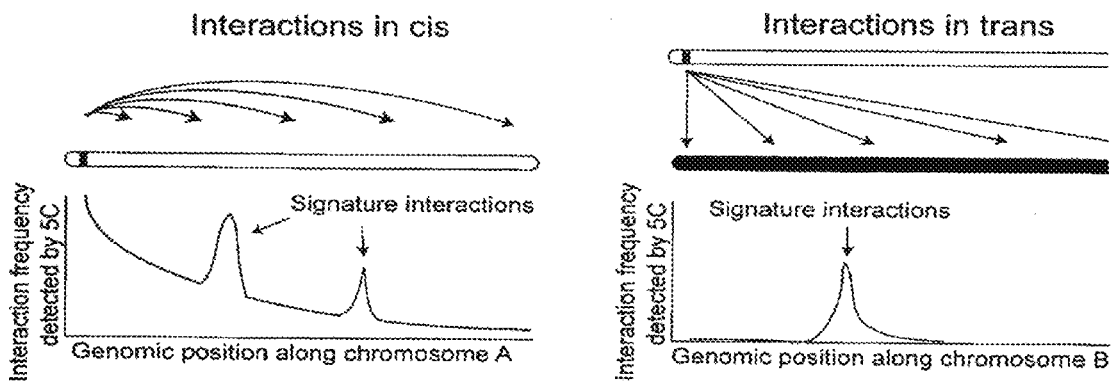

MAPPING OF GENOMIC INTERACTIONS

This application is a 371 of PCT/US2007/018745 filed Aug. 24, 2007 which claims benefit of provisional application 60/839,748 filed Aug. 24, 2006.

STATEMENT OF GOVERNMENTAL SUPPORT

This invention was supported by grants from the National Institutes of Health: NHGRI-ENCODE HG03143; NHGRI-ENCODE HG003129; and CA109597. Consequently, the United States government may have certain rights to the disclosed technology.

FIELD OF INVENTION

The present invention relates to genomic analysis. In particular, the present invention provides methods and compositions for mapping genomic interactions.

BACKGROUND

Efforts are underway to map genes and regulatory elements throughout the human genome. ENCODE-Consortium et al., Science 306:636-640 (2004). The goals of these efforts are to identify many different types of elements, including those involved in gene regulation. DNA replication and genome organization in general. However, currently thorough identification of genes and regulatory elements has only been performed for a selected 1% of the human genome.

In order to fully annotate the human genome and to understand its regulation, a complete gene map of all functional elements should also determine and define the relationships between them. For instance, for each gene it needs to be established by which elements it is regulated. This is complicated by the fact that the genomic positions of genes and elements do not provide direct information about functional relationships between them. A well-known example is provided by enhancers that can regulate multiple target genes that are located at large genomic distances or even on different chromosomes without affecting genes immediately next to them (Spilianakis et al., Nature 435: 637-645 (2005); and West et al., Hum Mol Genet. 14:R101-111 (2005)).

What is needed in the art is a high-throughput method that can isolate interactions between genes and gene regulatory elements as well as interactions between regulatory elements themselves combined with methods to quantify the occurrence of such interactions.

SUMMARY OF THE INVENTION

The present invention relates to genomic analysis. In particular, the present invention provides methods and compositions for mapping genomic interactions. For example, in some embodiments, the present invention provides chromosome conformation capture carbon copy (5C) methods for studying genomic interactions (e.g., genomic interactions involved in regulation of gene expression and global chromatin structure). The methods and compositions of the present invention find use in diagnostic and research applications.

Accordingly, in some embodiments, the present invention provides a method, comprising contacting a genomic interaction library (e.g., generated using the 3C or related method; for example the 3C method described by Dekker, et al (2002) Science 295:1306-1311) with a plurality of unique pairs of PCR primers under conditions such that ligation mediated amplification generates a second genomic interaction library; and amplifying the second genomic library with a single pair (or a limited number of pairs) of PCR primers, wherein the PCR primers amplify all members of the second genomic library. In some embodiments, the plurality of unique pairs of PCR primers comprises at least 10, preferably at least 100, more preferably at least 500, even more preferably at least 1000, yet more preferably at least 10,000 and still more preferably at least 100,000 unique pairs of PCR primers. In some embodiments, the second genomic interaction library comprises nucleic acids approximately 100 bps in length, although the present invention is not so limited. In some embodiments, members of the second genomic interaction library are identified and/or quantified using high throughput sequencing. In other embodiments, members of the second genomic interaction library are identified using a microarray. In still further embodiments, additional identification methods are employed, including, but not limited to, hybridization analysis, mass spectrometry analysis, etc. In some embodiments, the genomic interaction library comprises sequences involved in long range genomic interactions (e.g., interaction of activating or repressing chromatin elements with a gene or global genomic structures or interactions between locations on different chromosomes). In some embodiments, the genomic interaction library is derived from a cell (e.g., an animal (e.g., human) cell, a bacterial cell, a viral cell, or a plant cell). In certain embodiments, the method further comprises the step of calculating interaction frequencies for the long-range genomic interactions. In some embodiments, the genomic interaction library is derived from a cell that has one or more variant genes (e.g., polymorphisms (e.g., single nucleotide polymorphisms), genomic deletions, genomic fusions, genomic translocations, or genomic inversions).

The present invention further comprises a method, comprising: contacting a cell with a test compound; and generating a second genomic library from the cell using the method of the present invention, and comparing interaction frequencies in the second genomic library with interaction frequencies in a second genomic library generated from a cell not exposed to the test compound.

The present invention additionally comprises a method, comprising: contacting nucleic acid with a cross-linking agent under conditions such that interacting chromatin segments are cross-linked; digesting the cross-linked chromatin segments (e.g., with a restriction enzyme) to generate digested chromatin segments; ligating the digested chromatin segments to generate a genomic interaction library; contacting the genomic interaction library with a plurality of unique pairs of PCR primers under conditions such that ligation mediated amplification generates a second genomic interaction library; and amplifying the second genomic library with a single pair (or a limited set of pairs) of PCR primers, wherein the PCR primers amplify all members of the second genomic library.

In yet other embodiments, the present invention provides a kit, comprising a plurality of unique primers for performing ligation mediated amplification on a genomic interaction library. In some embodiments, the plurality of unique primers comprises at least 10, preferably at least 100, more preferably at least 500, even more preferably at least 1000, yet more preferably at least 10,000 and still more preferably at least 100,000 unique primers. In some embodiments, the kit comprises all of the components necessary or sufficient to generate and utilize a diagnostic signature or interaction profile (e.g., control signatures and instructions and/or software for comparing the diagnostic signature to a test sample). In some embodiments, the kit further comprises one or more of a polymerase (e.g., a thermostable DNA polymerase), a ligase (e.g., a thermostable ligase), primers for amplifying the products of a ligase chain reaction, buffers, control reagents, sequencing reagents, solid surfaces for analysis, microarrays for analysis, detection devices, software, instructions, and control genomic interaction libraries.

BRIEF DESCRIPTION OF THE FIGURES

FIG. 12 shows Table 3.
FIG. 13 shows Table 5.
FIG. 14 shows Table 6.
FIG. 15 shows Table 7.
FIG. 16 shows a schematic of mapping of chromosome rearrangements using 5C.
FIG. 17 shows exemplary diagnostic signatures of some embodiments of the present invention.

DEFINITIONS

Figure 1:
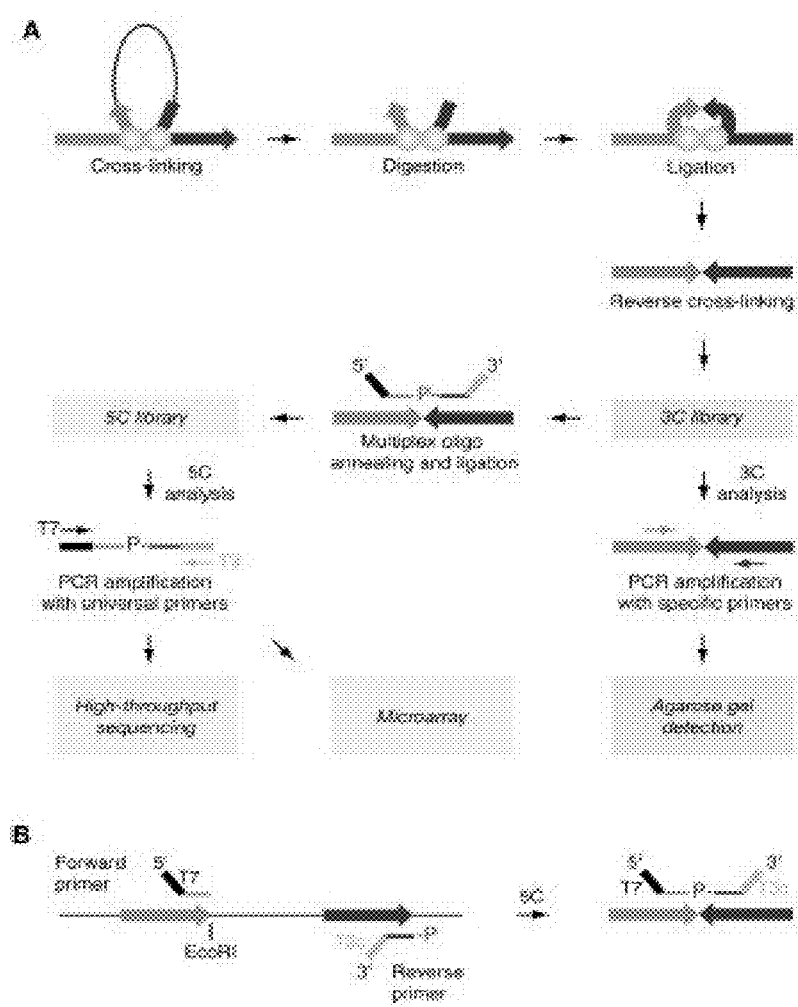
FIG. 1 shows a schematic representation of 5C. (A) A schematic of the generation of a 5C library from a 3C library (B) 5C primer design.

As used herein, the term "genomic interaction library" refers to a library of nucleic acids generated by long range genomic interactions (e.g., chromatin looping chromatin looping, and interactions between elements located on different chromosomes). In some embodiments, genomic interaction libraries are generated by chromosome conformation capture analysis methods described herein (e.g., the 3C methods described by Dekker, et al (2002) Science 295:1306-1311, herein incorporated by reference). In certain embodiments, genomic interaction libraries are further modified using the carbon copy ligation mediated amplification methods described herein. For example, in some embodiments, the genomic interaction library is copied using ligation mediated amplification, followed by PCR amplification to generate a second genomic interaction library.

As used herein, the term "long range genomic interaction" refers to physical interactions between segments of nucleic acid (e.g., chromatin) located at large genomic distances (e.g., on different genes, at different loci, or different chromosomes). Some long range genomic interactions involve interactions between regulatory elements (e.g., enhancers or repressors of gene expression). For example, some long-range genomic interactions involve interactions between regulatory elements and the gene being regulated. Other long-range interactions involve interactions between genes. Still other long range interactions involve elements that play general roles in chromosome conformation. As used herein, the term "large genomic distances" refers to nucleic acid separated by at least one function unit of nucleic acid (e.g., an intron, a gene, or a chromosome). Examples of nucleic acid separated by large genomic distances include, but are not limited to, nucleic acids located on different chromosomes, on different loci, or a gene and a regulatory region.

As used herein, the term "interaction frequency" refers to the frequency at which two segment of nucleic acid (e.g., chromatin) interact. In some embodiments, interaction frequencies are calculated by dividing the number of sequences obtained by the number of sequences obtained from a control dataset that represents random interactions. In some embodiments, interaction frequencies are calculated by dividing the signal obtained by hybridizing the second genomic interaction library to a microarray by the signal obtained by hybridization of a control library to the microarray. In some embodiments, interaction frequencies are normalized to control datasets.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained. The term "gene" can also refer to a DNA sequence that is transcribed into an RNA molecule that does not encode for a polypeptide.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be the to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to have on its 3' end a region that is "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

As used herein, the terms "hybridize" and "hybridization" refer to the annealing of a complementary sequence to the target nucleic acid (the sequence to be detected) through base pairing interaction (Marmur and Lane, Proc. Natl. Acad. Sci. USA 46:453 [1960] and Doty et al., Proc. Natl. Acad. Sci. USA 46:461 [1960]). The terms "annealed" and "hybridized" are used interchangeably throughout, and are intended to encompass any specific and reproducible interaction between an oligonucleotide and a target nucleic acid, including binding of regions having only partial complementarity and binding interactions that make use of non-canonical interactions for stability and/or specificity.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The term "non-canonical" as used in reference to nucleic acids indicates interactions other than standard, or "Watson-Crick" base pairing, including but not limited to G-T and G-U base pairs, Hoogstein interactions, triplex structures, quad-raplex aggregates, and multibase hydrogen bonding such as is observed within nucleic acid tertiary structures, such as those found in tRNAs.

The stability of a nucleic acid duplex is measured by the melting temperature, or "$T_m$." The $T_m$ of a particular nucleic acid duplex under specified conditions is the temperature at which on average half of the base pairs have disassociated.

The term "probe" as used herein refers to an oligonucleotide which forms a duplex structure or other complex with a sequence in another nucleic acid, due to complementarity or other means of reproducible attractive interaction, of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene vary in sequence from one another. A second mutant form of the structural gene may exist. This second mutant form varies in sequence from both the wild-type gene and the first mutant form of the gene.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like. As noted above, an oligonucleotide primer need not be perfectly complementary to a target or template sequence. A primer need only have a sufficient interaction with the template that it can be extended by template-dependent synthesis.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The terms "test compound" and "candidate compound" refer to any chemical entity, pharmaceutical, drug, and the like that is a candidate for use to treat or prevent a disease, illness, sickness, or disorder of bodily function. Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to genomic analysis. In particular, the present invention provides methods and compositions for mapping genomic interactions. Recent evidence indicates that regulatory elements can act over large genomic distances by engaging in direct physical interactions with their target genes or with other elements (Chambeyron et al., *Curr Opin Cell Biol.* 16:256-262 (2004); de Laat et al., *Chromosome Res.* 11:447-459 (2003); Dekker, J., *Trends Biochem. Sci.* 28: 277-280 (2003); and West et al., *Hum Mol Genet.* 14:R101-111 (2005). These observations indicate that the genome is organized as a complex three-dimensional network that is determined by physical interactions between genes and elements. The present invention is not limited to a particular mechanism. Indeed, an understanding of the mechanism is not necessary to practice the present invention. Nonetheless, it is contemplated that functional relationships between genes and regulatory elements can be determined by analysis of this network through mapping of chromatin interactions.

The development of 3C has greatly facilitated the detection and study of cis- and trans-interactions between genes and regulatory elements. Experiments conducted during the development of the present invention resulted in the development of 5C technology, an extension of 3C that expands the range of 3C applications by allowing comprehensive and large-scale mapping of chromatin interactions. Large-scale application of 5C provides information about relationships between genes and regulatory elements and can be used to identify novel regulatory elements and to reveal higher-order chromosome structural features.

Physical interactions between elements can be detected with the Chromosome Conformation Capture (3C) method (Dekker, J., *Trends Biochem. Sci.* 28: 277-280 (2003); Dekker et al., *Science* 295:1306-1311 (2002); Miele et al., "Mapping chromatin interactions by Chromosome Conformation Capture (3C). In: *Current Protocols in Molecular Biology* (ed. R. B. P. M. Ausubel, R. E. Kingston, D. D. Moore, J. G. Seidman, J. A. Smith, and K. Struhl), pp. 21.11.21-21.11-20. John Wiley & Sons, Hoboken, N.J. (2006); and Splinter et al., *Methods Enzymol.* 375:493-507 (2004). 3C employs formaldehyde cross-linking to covalently trap interacting chromatin segments throughout the genome. Interacting elements are then restriction enzyme digested and intra-molecularly ligated (FIG. 1A). The frequency with which two restriction fragments become ligated is a measure for the frequency with which they interact in the nucleus (Dekker et al., (2002), supra).

3C was initially used to study the spatial organization of yeast chromosome III (Dekker et al., (2002), supra), and has since been applied to the analysis of several mammalian loci such as the beta-globin (Palstra et al., *Nat Genet* 35:190-194 (2003); Tolhuis et al., *Locus. Mol Cell* 10:1453-1465 (2002); and Vakoc et al., *Mol. Cell* 17:453-462 (2005)), the T-helper type 2 cytokine (Spilianakis et al., *Nat Immunol.* 5:1017-1027 (2004)), the immunoglobulin kappa (Liu et al., *Mol Cell Biol.* 25:3220-3231 (2005)), and the Igf2 imprinted locus (Murrell et al., *Nat Genet.* 36:889-893 (2004)). These studies revealed direct interactions between enhancers and promoters of target genes, with the linking DNA looping outward. 3C was also used to detect trans-interactions between yeast chromosomes (Dekker et al., (2002), supra) and between functionally related elements located on different mouse chromosomes (Ling et al., *Science* 312:269-272 (2006); Spilianakis et al., *Nature* 435: 637-645 (2005); Xu et al., *Science* 311:1149-1152 (2006)). Together, these studies indicate that long-range cis- and trans interactions play wide-spread roles in the regulation of the genome and that 3C is a convenient approach to map this network of interactions. 3C employs PCR to detect individual chromatin interactions, which is particularly suited for relatively small-scale studies focused at the analysis of interactions between a set of candidate elements. However, PCR detection is not conducive to ab initio and large-scale mapping of chromatin interactions. To overcome this problem, 3C libraries need to be analyzed using a high-throughput detection method such as microarrays or DNA sequencing. The extreme complexity of the 3C library, and the low relative abundance of each specific ligation product make direct large-scale analysis difficult.

The 3C method has been described in detail (Dekker, J., *Nat Methods* 3:17-21 (2006); Dekker et al., (2002), supra; Miele et al., supra; Splinter et al., *Methods Enzymol.* 375:493-507 (2004); and Vakoc et al., *Mol. Cell* 17:453-462 (2005)) and is illustrated in FIG. 1A. A 3C experiment generates a complex library of ligation products that reflects all chromatin interactions that occur throughout the genome. The abundance of each specific ligation product in the library is a measure for the frequency of interaction of the two corresponding loci.

In a typical 3C analysis individual interaction frequencies are determined by quantifying the formation of predicted "head-to-head" ligation products using semi quantitative PCR (FIG. 1A). As a PCR control, a library is used that contains all ligation products in equimolar amounts. The control library is generated by mixing equimolar amounts of minimally overlapping BAC clones covering the genomic region of interest (Dekker, J., *Nat Methods* 3:17-21 (2006); and Palstra et al., *Nat Genet* 35:190-194 (2003)). This mixture is then digested and randomly ligated. Interaction frequencies are determined by calculating the ratio of PCR product obtained with the 3C library and the amount obtained with the control library.

I. Chromosome Conformation Capture Carbon Copy (5C)

Experiments conducted during the course of development of the present invention resulted in the development of a novel methodology for large-scale parallel detection of chromatin interactions (e.g., interaction between different chromosomes, different genes or different loci). This method is called 3C-Carbon Copy or "5C". 5C employs highly multiplexed ligation-mediated amplification (LMA) to first "copy" and then amplify parts of the 3C library followed by detection on microarrays, by quantitative DNA sequencing, or by other suitable methods. 5C was developed and validated by analysis of the human beta-globin locus as well as a highly conserved genomic region located on human chromosome 16. However, the present invention is not limited to the analysis of a particular chromosome or locus. Results indicated that 5C quantitatively detects several known DNA looping interactions. 5C analysis also identified a looping interaction between the beta-globin Locus Control Region (LCR) and the gamma-delta intergenic region. Previously, several lines of evidence have suggested that this region plays a role in regulating the developmentally controlled switching from gamma-globin expression in fetal cells to beta-globin expression in adult cells (Calzolari et al., *EMBO J.* 18: 949-958 (1999); Gribnau et al., *Mol Cell.* 5:377-386 (2000).

5C is widely applicable to determine the cis- and trans-connectivity of regulatory elements throughout large genomic regions. In addition, in some embodiments, 5C experiments are designed so that complete interaction maps can be generated for any large genomic region of interest, which can reveal locations of novel gene regulatory elements and provide detailed insights into higher order chromosome folding. 5C can be used to detect, in a single reaction, a particular set of chromatin interactions that can provide diagnostic, predictive, or prognostic information.

Exemplary embodiments of 5C are described below. 5C analysis finds many uses and one skilled in the art recognizes that additional embodiments and applications of 5C are within the scope of the present invention.

A. Outline of the 5C Technology

In some embodiments, 5C technology detects ligation products in 3C libraries by multiplex LMA (FIG. 1A). LMA is widely used to detect and amplify specific target sequences using primer pairs that anneal next to each other on the same DNA strand (FIG. 1) (Landegren et al., *Science* 241: 1077-1080 (1988); Li et al., *Nucleic Acids Res.* 33:e168 (2005)). Only primers annealed next to each other can be ligated. Inclusion of universal tails at the ends of 5C primers allows subsequent amplification of ligated primers. LMA-based approaches are quantitative and can be performed at high levels of multiplexing using thousands of primers in a single reaction (Bibikova et al., *Genome Res.* 16:383-393 (2005); Fan et al., *Genome Res.* 14:878-885 (2004); Hardenbol et al., *Genome Res.* 15:269-275 (2005); Wang et al., *Nucleic Acids Res.* 33:e183 (2005).

In some embodiments, to analyze chromatin interactions by 5C, a 3C library is first generated using a conventional 3C method. A mixture of 5C primers is then annealed onto the 3C library and ligated. Two exemplary types of 5C primers are used: 5C forward and 5C reverse primers. In preferred embodiments, these primers are designed so that forward and reverse primers anneal across ligated junctions of head-to-head ligation products present in the 3C library (FIGS. 1A and B). 5C primers that are annealed next to each other are then ligated (e.g., with Taq ligase). This step generates a 5C library, which is amplified with universal PCR primers that anneal to the tails of the 5C primers.

In some embodiments, the products of ligation mediated amplification are further amplified using PCR. In preferred embodiments, the second, PCR based amplification utilizes a single pair of primers that anneal to the 5C ligation mediated amplification primers. In other embodiments, two or more pairs of PCR primers may be used, preferably a limited number of pairs (e.g., 2, 3, 4, 5) but preferably less than the number of ligation mediated amplification products.

Forward and reverse 5C primers are only ligated when both are annealed to a specific 3C ligation product. Therefore, the 3C library determines which 5C ligation products are generated and how frequently. As a result the 5C library is a quantitative "carbon copy" of a part of the 3C library, as determined by the collection of 5C primers.

Forward and reverse 5C primers are designed to contain a unique sequence corresponding to the sense and anti-sense strand of the 3'end of restriction fragments, respectively (FIG. 1B). The primers also contain universal tails for amplification (e.g., T7 at the 5' end of forward primers and T3c at the 3' end of reverse primers). The 5C technology is not limited to use of these tails, other tail sequences can be used dependent on possible requirements of downstream detection methods. To analyze interactions between many restriction fragments, multiple forward and reverse primers are mixed together in the same multiplex 5C reaction. Since predicted forward and reverse primers of each restriction fragment are complementary, only one primer per fragment, either a forward or a reverse, is used in a given 5C experiment. In some embodiments, to facilitate ligation, all reverse primers are phosphorylated at their 5' end. This 5C primer design allows simultaneous amplification of all potential interactions between all restriction fragments recognized by a forward primer and all those recognized by a reverse primer.

5C utilizes multiplexed ligation mediated amplification. Other assays based on LMA have successfully used many thousands of primers in a single reaction. For example, methylation status of 1534 CpG sites was assessed using a mixture of ~6000 primers (Bibikova et al., *Genome Res.* 16:383-393 (2005)). Another example is the use of highly multiplexed LMA with up to 20,000 Molecular Inversion Probes in a single reaction to detect single nucleotide polymorphisms (SNPs) (Hardenbol et al., *Genome Res.* 15:269-275 (2005); and Wang et al., *Nucleic Acids Res.* 33:e183 (2005)). When 5C is performed at a similar level of multiplexing, e.g. using 10,000 5C primers in a single experiment, up to 25 million distinct chromatin interactions can be detected in parallel involving up to 40 Mb (10,000 4 kb restriction fragments) of DNA.

For highly multiplexed 5C analyses, it is preferred to carefully design 5C primers. Nine 5C primers that were used to generate the 5C libraries analyzed during experiments conducted during the development of the present invention perfectly recognized abundant interspersed repeats and these primers were found to produce excessively large numbers of ligation products (see Table 5B). Thus, it is preferred that repeated sequences be avoided.

In some embodiments, 5C applications are high-throughput applications. As described above, 5C methods are conducive to high levels of multiplexing. For example, in some embodiments, 10, preferably 100, even more preferably 500, still more preferably 1000, yet more preferably 10,000 and even more preferably 100,000 primers are utilized in 5C applications. In some embodiments, high-throughput methods such as the use of microtiter plates are utilized for the simultaneous analysis of many different samples.

The products of a 5C reaction (5C library) may be analyzed using any suitable method. In some exemplary embodiments of the present invention, 5C libraries are detected using high throughput sequencing or microarray (See e.g., the Experimental section below). However, 5C libraries may be detected using any DNA detection method including, but not limited to, bead based detection methods, mass spectrometry, and other detection methods known to those in the art.

5C methods are suitable for use with any number of cell types (e.g., including, but not limited to, animal (e.g., human), plant, bacteria, fungi, and other organisms.

In some embodiments. 5C methods are automated. For example, in some embodiments, all of the steps of the 5C method (e.g., sample prep, 5C methods, and analysis of 5C libraries) are automated. In some embodiments, robotic methods are utilized.

B. Chromatin Looping in the Human Beta-Globin Locus

Figure 2:
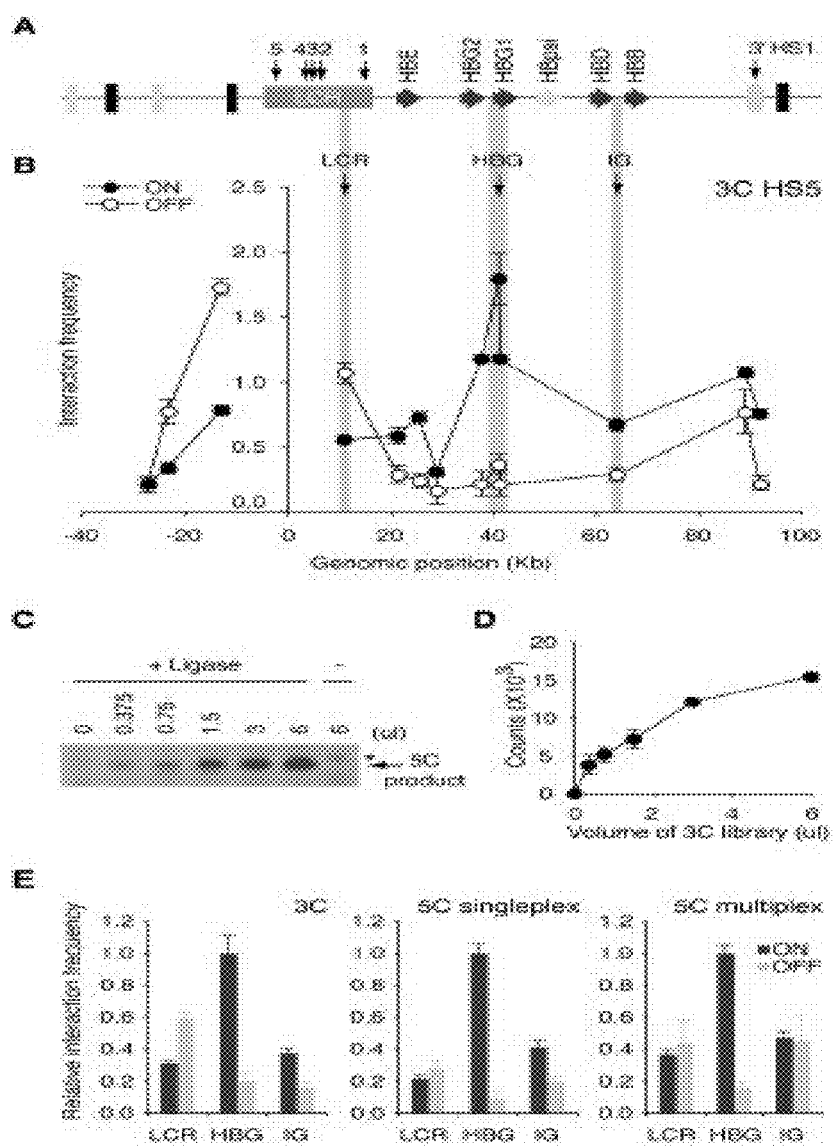
FIG. 2 shows analysis of the human beta-globin locus and development of 5C. (A) Schematic representation of the human beta-globin locus. (B) 3C analysis of interactions between the LCR (HS5) and the rest of the beta-globin locus. (C) Representative 3C library titration in singleplex LMA with 5C primers. (D) Quantification of titration shown in (C). Each datapoint corresponds to the average of 3 PCR reactions; error bars represent s.e.m. (E) 3C, singleplex and 6-plex LMA detection of looping interactions between HS5 and the A gamma-globin gene HBG1.

Experiments conducted during the course of developments of the present invention optimized the 5C approach by analysis of the human betaglobin locus. However, the present invention is not limited to a particular genomic region. One skilled in the relevant arts recognizes that the 5C technology of the present invention finds use in the analysis of any number of loci or genomic regions. This locus was selected because several looping interactions have previously been detected by 3C as well as by a second method, RNA-TRAP (Carter et al., *Nat. Genet.* 32: 623-626 (2002); and Tolhuis et al., *Locus. Mol Cell* 10:1453-1465 (2002)). The human beta-globin locus consists of five developmentally regulated beta-globin-like genes (epsilon (HBE); A gamma and G gamma (HBG1 and HBG2), delta HBD) and beta (HBB)), one pseudogene (Hbpsi), and a Locus Control Region (LCR) located upstream of the gene cluster (FIG. 2A). The LCR is characterized by five DNAse I hypersensitive sites (HS1-5) and is required for tissue-specific and position independent expression of downstream beta-globin genes (Li et al., *Blood* 100:3077-3086 (2002); and Stamatoyannopoulos, *Exp Hematol.* 33:256-271 (2005). Previous 3C analysis of the murine beta-globin locus revealed transcription factor-mediated looping interactions between the LCR and transcribed globin genes (Drissen et al., *Genes Dev.* 18:2485-2490 (2004); and Vakoc et al., *Mol. Cell* 17:453-462 (2005). The LCR was also found to interact with HS elements located upstream (HS-62.5/HS-60) and downstream (3'HS1) of the locus (Tolhuis et al., *Locus. Mol Cell* 10:1453-1465 (2002).

Experiments conducted during the course of development of the present invention resulted in the detection of chromatin looping interactions in the human beta-globin locus by 5C. The most prominent interaction was observed between the LCR and the expressed gamma-globin genes specifically in K562 cells. In both K562 and GM06990 cells the LCR also interacted with the 3'HS1 element and a large domain located 50-100 kb upstream. The latter region corresponds to the region around HS-62.5/HS-60 in the murine locus that has been shown to interact with the murine LCR (Tolhuis et al., *Locus. Mol Cell* 10:1453-1465 (2002). Similar long-range interactions between HSs were observed in the mouse. Although the functional significance of some of these interactions is not well understood, the clustering of HSs is thought to create a chromatin hub, or a specialized nuclear compartment dedicated to the transcription of the beta-globin genes (de Laat et al., *Chromosome Res.* 11:447-459 (2003); and Tolhuis et al., *Locus. Mol Cell* 10:1453-1465 (2002)).

Several of the HSs in the beta-globin locus bind the insulator binding protein CTCF (Bulger et al., *Mol Cell Biol.* 23: 5234-5244 (2003); Farrell et al., *Mol. Cell Biol.* 22:3820-3831 (2002)) and for human HS5 see FIG. 10) and this protein as been proposed to mediate their interactions and the formation of the chromatin hub (Patrinos et al., *Genes Dev.* 18:1495-1509 (2004)). The pattern of interactions between the LCR and the rest of the beta-globin locus in the blood-derived GM06990 cells is similar to those observed in K562, except that all interaction frequencies are significantly lower. The present invention is not limited to a particular mechanism. Indeed, an understanding of the mechanism is not necessary to practice the present invention. Nonetheless, it is contemplated that the locus is in a "poised state" in which several chromatin looping interactions, e.g. those between the LCR and 3' HS1 and the upstream HS elements are already established prior to beta-globin expression, as has been suggested for the murine locus (Palstra et al., *Nat Genet* 35:190-194 (2003)).

Figure 10:
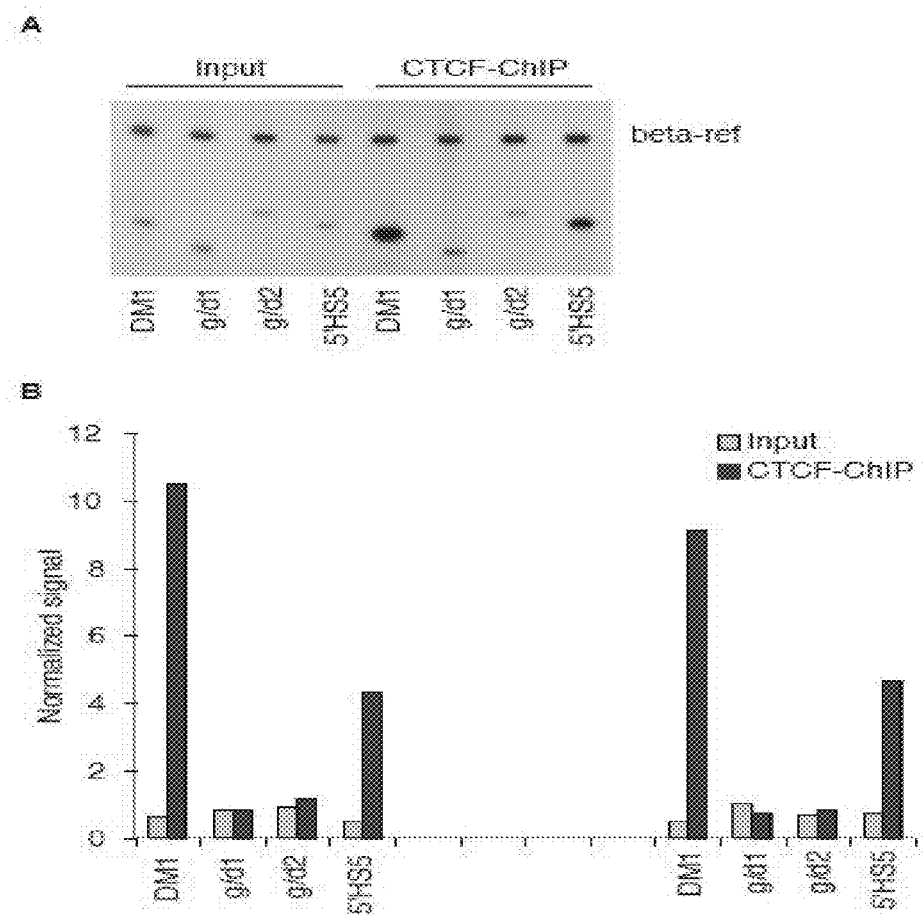
FIG. 10 shows analysis of CTCF binding to sites within the gamma-delta intergenic region (g/d1, g/d2) and the LCR (5'HS5) of the beta-globin gene locus in K562 cells. (A) Result of a representative quantitative duplex PCR with DNA recovered from a ChIP with antibodies to CTCF. (B) Quantitative results of two independent replicate ChIP experiments.

The interaction profiles of HS5 and HS2/3/4 are very similar, except that HS2/3/4 interacted more frequently with the beta-globin locus specifically in K562 cells. This result is in agreement with observations that HS2 and HS3 have the strongest enhancer activity (Fraser et al., *Genes Dev.* 7:106-113 (1993); and Peterson et al., *Proc Natl Acad Sci USA.* 93: 6605-6609 (1996)). In addition, RNA-TRAP found that the expressed globin gene interacted most strongly with HS2 (Carter et al., *Nat. Genet.* 32: 623-626 (2002)). A new chromatin looping interaction between the LCR and the region between the gamma- and delta-globin genes was identified. This region has been implicated in developmental control of the beta-globin (Chakalova et al., *Blood* 105: 2154-2160 (2005); and O'Neill et al., *Proc Natl Acad Sci USA.* 96:349-354 (1999)). This region contains a promoter for a large intergenic transcript, whose expression may be related to activation of the adult beta-globin gene (Gribnau et al., *Mol Cell.* 5:377-386 (2000)). Certain patients that suffer from hereditary persistence of fetal hemoglobin carry deletions in this region and display defects in beta-globin expression (Chakalova et al., *Blood* 105: 2154-2160 (2005)). In contrast to some other looping interactions in the locus, CTCF may not to play a role in the interaction between the LCR and the gamma-delta intergenic regions, CTCF binding to several sites within the intergenic region was not detected, despite the presence of several weak putative CTCF binding sites (FIG. 10).

Figure 3:
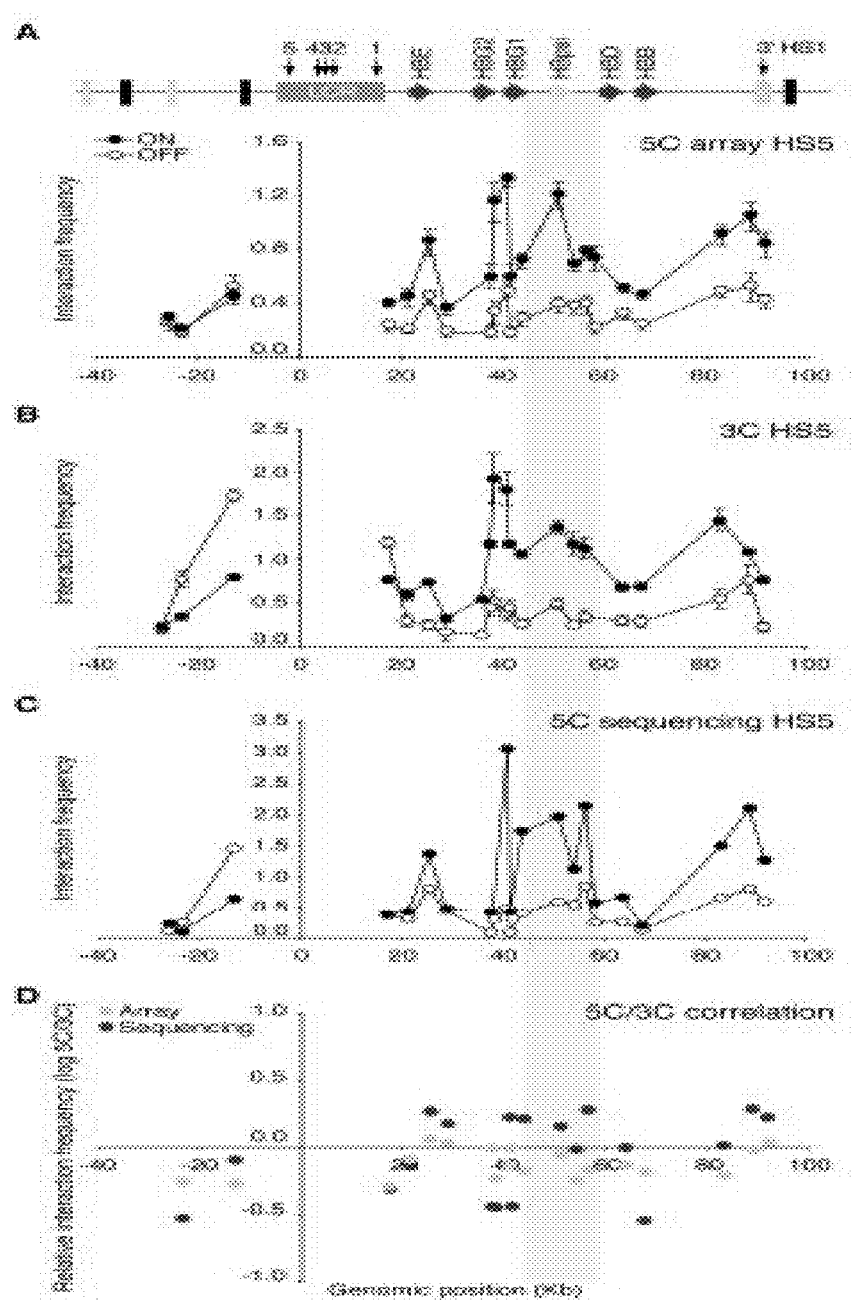
FIG. 3 shows that microarray and DNA sequencing analysis of 5C libraries recapitulate 3C interaction profiles. (A) 5C analysis of human beta-globin locus HS5 chromatin interactions in K562 (ON) and GM06990 (OFF) cells detected by microarray. (B) Conventional 3C analysis of human beta-globin HS5 chromatin interactions. (C) 5C analysis of human betaglobin HS5 interactions as detected by quantitative DNA sequencing. (D) Correlation between 3C and 5C human beta-globin locus profiles from K562 cells.
Figure 4:
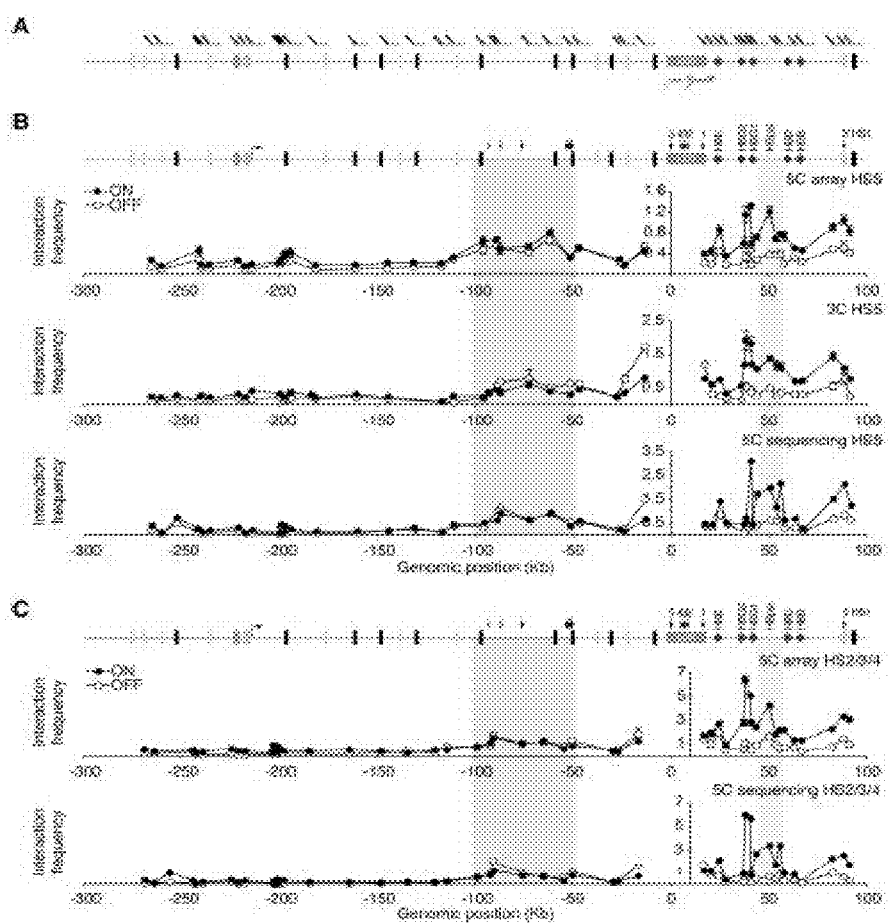
FIG. 4 shows large-scale 5C analysis of the human beta-globin locus. (A) Positions of forward (top) and reverse (bottom) 5C primers within the beta-globin locus (B) Chromatin interaction profile of HS5 with a 400 kb region surrounding the LCR. Physical interactions in K562 (ON) and GM06990 (OFF) cells were measured by 5C and microarrays (top), 3C (middle), and 5C and quantitative sequencing (bottom) analysis. (C) Chromatin interaction profile of HS2/3/4 of the LCR with the 400 kb region around the LCR as determined by microarray (top), and quantitative sequencing (bottom).

Results obtained with microarray detection, quantitative sequencing and semiquantitative PCR are generally very comparable. Several differences were observed. First, the dynamic range of microarray detection was smaller than that of quantitative sequencing, as has been observed before (Yuen et al., *Nucleic Acids Res.* 30:e48 (2002)). Second, small quantitative differences were observed between the data sets obtained by microarray analysis, quantitative sequencing and semi-quantitative PCR, e.g. in the gamma-delta intergenic region (FIGS. 3 and 4). The present invention is not limited to a particular mechanism. Indeed, an understanding of the mechanism is not necessary to practice the present invention. Nonetheless, it is contemplated that these differences reflect intrinsic biases in the detection methods or experimental variation between independently generated 5C libraries. DNA sequencing displays a larger dynamic range and obviates the need to design a specific array for each genomic region of interest. Microarray analysis is currently more cost effective, particularly when a given genomic region needs to be analyzed under a large number of different conditions. 5C data obtained by DNA sequencing allowed an estimate of the background of the LMA-based approach. 451 interactions between the beta-globin locus and the control gene desert region, which are located on different chromosomes, were quantitated. These interactions are detected by forward primers located on one chromosome and reverse primers located on the other and vice versa. There is no biological indication that the beta-globin locus and the gene desert region should preferentially interact. Therefore it is contemplated that these inter-chromosomal interaction frequencies correspond to background signals. Very low background interaction frequencies between the two regions were detected (average interaction frequency 0.08, (s.e.m.=0.02) for K562 and 0.08 (s.e.m=0.01) for GM06990; Table 6), which is 75-fold lower than the interaction frequency between HS2/3/4 and the gammaglobin gene in K562 cells. A few higher interaction frequencies were detected that could reflect true trans-interactions between the two genomic regions.

C. Mapping of Looping Interactions

Transcription regulation in higher eukaryotes is controlled by regulatory elements such as enhancers that are recognized by transcription factors. In many cases regulatory elements can be located at distances up to several megabases from their target genes. Recent evidence shows that long-range control of gene expression can be mediated through direct physical interactions between genes and these regulatory elements. In some embodiments, 5C is used for large-scale mapping of chromatin looping interactions between specific genomic elements of interest (e.g., the beta-globin locus). In certain embodiments, such studies are focused at mapping interactions between a "fixed" element, e.g. the LCR, and other restriction fragments located in cis or in trans in order to identify elements that it interacts with. 5C allows simultaneous quantification of interaction profiles of many such "fixed" elements in parallel in a single reaction followed by analysis on a custom-designed microarray or by direct quantitative sequencing. To do this, reverse 5C primers are designed for each fixed fragment of interest and forward 5C primers are designed for all other restriction fragments, as shown in FIG. 4A. This type of analysis allows rapid detection of networks of interactions among multiple genes and regulatory elements throughout large segments of the genome.

D. Interaction Maps

In other embodiments, 5C analysis is used to generate dense interaction maps that cover most or all potential interactions between all fragments of any genomic region. Dense interaction maps provide a global overview of the conformation of a given genomic region. For example, when 5C forward and reverse primers are designed for alternating restriction fragments, as performed during the course of development of the present invention for the gene desert control region (FIG. 5), a relatively dense matrix of interaction frequencies is quickly obtained throughout a genomic region.

In some embodiments, several 5C analyses, each with a permutated 5C primer design scheme are performed to obtain partially overlapping interaction matrices. Such analyzes provide a complete interaction map for a given genomic region, as interactions between two fragments that are both recognized by forward primers or reverse primers cannot be detected. When combined these maps yield complete interaction maps containing interaction frequencies of all pairs of restriction fragments throughout a region of interest. Each row and column of such matrices corresponds to a "fixed" element experiment as described above. Generation of complete interaction matrices finds use as a discovery tool for unbiased detection of chromatin looping interactions between previously unannotated elements. Analysis of a matrix of interaction frequencies provides global information regarding the general spatial conformation of a genomic region (Dekker et al., (2002)).

In some embodiments, the spatial conformation of a genomic region is compared before and after induction of gene expression or silencing. Such embodiments find use in research, diagnostic, and therapeutic (e.g., drug screening) applications.

III. 5C Applications

The 5C methods of the present invention find use in a variety of research, diagnostic, and clinical applications. Exemplary applications are described below.

A. Drug Screening

In some embodiments, the 5C technology of the present invention finds use in drug screening applications. For example, in some embodiments, 5C analysis is used to detect the three dimensional structure of a genomic region in the presence and absence of a test compound. In other embodiments, 5C is used to detect looping interactions between regulatory region in the presence and absence of test compounds. Such embodiments find use in the study of drug function and in the identification of compounds that alter the expression of a target gene. Such embodiments further find use in the identification and study of compounds that alter chromosome conformation and chromatin looping interactions.

B. Diagnostic Applications

In other embodiments, the 5C technology of the present invention finds use in diagnostic applications. For example, in some embodiments, 5C methods are used to determine the status of chromosome conformation of a gene of interest and identify cis- and trans chromatin interactions it is involved in. Certain disease states are characterized by aberrant (e.g., increased or decreased) gene expression that correlates at some states of development or in some cell types with distinct pattern of chromatin interactions. 5C methods thus find use in the diagnosis of such disease states by detecting these patterns of chromatin interactions. In some embodiments, 5C is used to compare the interaction profiles of genes in the activated or inactivated states with test samples in order to determine the activation status of a gene.

In still other embodiments, 5C is used in the detection of variant (e.g., polymorphic) genes that have altered expression. For example, in some genes the presence of certain single nucleotide polymorphisms (SNPs) are associated with disease states or altered gene function (e.g., drug metabolism). In some embodiments, 5C is used to compare the interaction profile of known SNPs with test samples in order to determine the chromatin interactions of the variant gene, which can in some case be correlated with the activation status of a gene at some stage of development or in some cell types.

In yet other embodiments, 5C is used to detect patterns of chromatin interactions that are indicative of genomic rearrangements including, but not limited to, translocation, deletion, fusion, and inversion. In some embodiments, 5C is used to compare the interaction profile of known gene rearrangements with test samples in order to determine the chromatin interactions of the variant gene, which can in some case be correlated with the activation status of a gene at some stage of development or in some cell types. FIG. 16 shows an overview of the predicted interaction profile for some exemplary genomic rearrangements. In some embodiments, interaction profiles to be used as controls are experimentally generated using, for example, the methods of the present invention.

In additional embodiments, diagnostic signatures are utilized. In some embodiments, diagnostic signatures give information about diagnostic predisposition and prognosis regarding specific diseases. For example, in some embodiments, diagnostic signatures predict future genomic rearrangements or detect chromosome conformation features (e.g., looping or trans-interactions) associated with particular disease states or prognosis. Exemplary diagnostic signatures are shown in FIG. 17. In some embodiments, diagnostic signatures to be used as controls (e.g., indicative of a given disease state or prognosis) are experimentally generated using, for example, the methods of the present invention.

C. Research Applications

In yet other embodiments, the 5C methods of the present invention find use in research applications. Such applications include, but are not limited to, the study of gene regulation in development and differentiation, the study of gene regulation in disease, the study of gene regulation in drug metabolism, and the study of regulation of variant genes. In some embodiments, research applications utilize samples from human subjects. In other embodiments, research applications utilize test samples from non-human animals (e.g., non-human mammals). In some embodiments, the non-human animals are transgenic animals.

D. Kits

In yet other embodiments, the present invention provides kits for performing 5C. In some embodiments, the kits contain all of the components necessary or sufficient for performing 5C analysis to detect particular patterns of chromatin interactions in cells, including all controls, directions for performing assays, and any software for analysis and presentation of results. In some embodiments, the kits contain primers for performing 5C analysis. In some embodiments, the kits comprise all materials necessary or sufficient to perform 5C in a single reaction and provide diagnostic, prognostic, or predictive information (e.g., to a researcher or a clinician). In some embodiments, the kits comprise one or more of a polymerase (e.g., a thermostable DNA polymerase), a ligase (e.g., a thermostable ligase), primers for amplifying the products of a ligase chain reaction, buffers, control reagents, sequencing reagents, solid surfaces for analysis, microarrays for analysis, detection devices, software, instructions, and control genomic interaction libraries.

In some embodiments, the kits comprise all of the components for generating and utilizing a diagnostic signature (e.g., to provide a diagnosis or prognosis) or interaction profile of a sample. For Example, in some embodiments, the kits comprise control diagnostic signatures or interaction profiles and software and/or instructions for comparing a test sample to the control.

EXPERIMENTAL

The present invention provides the following non-limiting examples to further describe certain contemplated embodiments of the present invention.

Example I

General Laboratory Methods

BAC selection and control library preparation. A control library for the human betaglobin locus and gene desert regions (ENCODE regions ENm009 and ENr313, respectively) was generated as described (Dekker, J., Nat Methods 3:17-21 (2006); and Miele et al., supra). Briefly, an array of bacterial artificial chromosomes (BACs) covering both genomic regions was mixed, digested with EcoRI, and randomly ligated. In this study, the BAC arrays from the beta-globin locus and gene desert regions were mixed in a 4:1 ratio, to obtain strong signals for the beta-globin locus. Interaction frequencies were adjusted accordingly. The following 7 BAC clones were used for the beta-globin region: CTC-775N13, RP11-715G8, CTD-3048C22, CTD3055E11, CTD-264317, CTD-3234J1, and RP11-589G14. A set of 4 BAC clones was selected to cover the 0.5 Mb gene desert region, and include RP11-197K24, RP11-609A13, RP11-454G21, and CTD-2133M23. BAC clones were obtained from Invitrogen and the Children's Hospital Oakland Research Institute (CHORI).

Cell culture and 3C analysis. The GM06990 cell line was derived from EBV transformed B-lymphocytes and was obtained from Coriell Cell Repositories (CCR). This cell line was cultured in Roswell Park Memorial Institute medium 1640 (RPMI 1640) supplemented with 2 mM L-glutamine and 15% fetal bovine serum (FBS). The K562 cell line was obtained from the American Type Culture Collection (ATCC) and cultured in RPMI 1640 supplemented with 2 mM L-glutamine and 10% FBS. Both cell lines were grown at 37° C. in 5% $CO_2$ in the presence of 1% penicillin-streptomycin. 3C analysis was performed with log phase GM06990 and K562 cells using EcoRI as previously described (Dekker et al., Science 295:1306-1311 (2002); Miele et al., supra; Vakoc et al., Mol. Cell 17:453-462 (2005)). Primer sequences are presented in Table 2.

Real-time PCR quantification. Total RNA from log phase cells was isolated with the RNeasy Mini Kit as described by the manufacturer (Qiagen). cDNA was synthesized with oligo(dT)$_{20}$ (Invitrogen) using the Omniscript Reverse Transcription Kit (Qiagen). Beta-globin transcripts were quantified by real-time PCR in the presence of SYBR Green I stain (Molecular Probes). Specific human beta-globin primers used in this analysis are summarized in Table 1.

TABLE 1

| GENE NAME | PRIMER NAME | PRIMER SEQUENCE (5'-3') |
|---|---|---|
| HBE (EPSILON) | FORWARD HBE | GCTATTAAAAACATGGACAACCTC |
| | REVERSE HBE | CTCAGTGGTACTTATGGGCCAGG |
| HBG1,2 (GAMMA 1,2) | FORWARD HBG1AND2 | GCACCTGGATGATCTCAAGGG |
| | REVERSE HBG1AND2 | GCTTGCAGAATAAAGCCTATCC |
| HBpsi (PSEUDOGENE) | FORWARD HBpsi | CGGAAAAGCTGTTATGCTCACGG |
| | REVERSE HBpsi | CCATCTAAAGGAGATGAGATTTTGGG |
| HBD (DELTA) | FORWARD HBBandD | GCCTTTAGTGATGGCCTGGCTCACC |
| | REVERSE HBD | GGAAACAGTCCAGGATCTCAATG |
| HBB (BETA) | FORWARD HBBandD | GCCTTTAGTGATGGCCTGGCTCACC |

TABLE 1-continued

| GENE NAME | PRIMER NAME | PRIMER SEQUENCE (5'-3') |
|---|---|---|
| | REVERSE HBB | GGACAGCAAGAAAGCGAGCTTAGTG |

TABLE 2

| PRIMER NAME | SEQUENCE (5'-3') | EcoR1 FRAGMENT POSITION START | END | FRAGMENT NAME |
|---|---|---|---|---|
| 1. BETA-GLOBIN LOCUS (ENm009) CHROMOSOME 11 | | | | |
| GP98 | AGCACCATGGCATAGATTGAGGAGAAGG | 5175267 | 5178450 | 131 |
| GPF10 | TCTACACTCTCAGTCAGCCTATGGAACC | 5178451 | 5184169 | 132 |
| GPF11 | CAGGAGGTTGCCTTTGCTGTGGCTTTCGACCC | 5184170 | 5165420 | 133 |
| GPF14 | GAAAGCGAGCTTAGTGATACTTGTGGGC | 5199709 | 5203476 | 136 |
| GPF15 | GCTCCCACACTCCTAGACTCTTACAAAAGC | 5203479 | 5209033 | 137 |
| GPF17 | CGAAGTTCCTGGGAATATGCTAGTACAGAAC | 5210845 | 5213155 | 139 |
| GPF18 | GAATATTGAGATGATATATGCACAGAACAATGCC | 5213108 | 5216308 | 140 |
| GPF19 | CATGTCCTTTAATGGCCCTAAAACTCATTCCC | 5218307 | 5223331 | 141 |
| GPF20 | GAAATGCTGTGACCAATCTGCACACTTGAGG | 5223332 | 5225884 | 142 |
| GPF21 | GCCTATCCTTGAAAGCTCTGAATCATGGGC | 5225685 | 5226239 | 143 |
| | | 5229577 | 5231157 | 145 |
| GPF22 | GGACCATTAACAGGGTAGGAAGTATTTATGG | 5226240 | 5226681 | 144 |
| GPF23 | GGGCATGTGGAAACTCTGAGGCTGAGG | 5228882 | 5119578 | 146 |
| GPF25 | CAGAGTATCCAAAGTTATCTAAAGACAAAGAGAATC | 5231158 | 5238141 | 147 |
| GPF27 | GATATATAGACCAGTGGAACAGAACAGAAGCC | 5236403 | 5239933 | 149 |
| GPF30 | CAGGTACCACTAACAGCTCCTTCTTTCC | 5251811 | 5245997 | 152 |
| GPF31 | CCAGAAGTCTTCACCTGACTTAATGACTGCCC | 5245998 | 5249755 | 153 |
| GPF32 | GACATCAAGTATTTCTTGGATGCTGACCAGAGG | 5249758 | 5256287 | 154 |
| GPF33 | GACCTCTGCACTAGGAATGGAAGGTTAGCC | 5258268 | 5256610 | 155 |
| GPF35 | TCCTTGCAAATCATGAATAATGATCAATCGAGG | 5267231 | 5270591 | 157 |
| GPF36 | GGTGAGGAAATTGAGCCTTAGACAAGTTAAGC | 5270592 | 5283838 | 158 |
| GPF38 | GTACATAGTTAACCTGCTGCTTAGCTTATTTGC | 5285015 | 5294021 | 160 |
| GPF41 | GGCTGAGAGTCAAATCGAGAACACAATCC | 5298304 | 5298001 | 163 |
| GPF47 | GGCACCATGAAATTTATTCCTCATGAGGTCC | 5310481 | 5317144 | 169 |
| GPF48 | CTGCACATTCCAGGATCTATCTCCTACCTACG | 5317145 | 5321683 | 170 |
| GPF55 | GACCCATGTCTTTCTGTGTGTCTGCTAGTTC | 5329232 | 5332065 | 177 |
| GPF56 | GAAGGCTACAAGGGGATTTCTCAAGTAACTGC | 5332056 | 5342910 | 178 |
| GPF57 | GACATTGCTCAAGGTTAGCTAAAGATATG | 5342911 | 5357573 | 179 |
| GPF58 | GGTACACTGTTACAGTGACACTTTTCAC | 5357574 | 5359095 | 180 |
| GPF59 | GACAACAGAACCCCAGGCACAAAGAATCAGG | 5359068 | 5363389 | 181 |
| GPF60 | CCAATGATATGGTGGCTAAAAAGTCAATCCC | 5363370 | 5366062 | 182 |
| GPF64 | GTGTAATGGGAAATCTATTGAGCCCTCTGTGC | 5377148 | 5381758 | 186 |
| GPF67 | CAATAGAGGAAAAGGAGGTACAGAAGCAC | 5383984 | 5387568 | 189 |
| GPF76 | CAGTTATCCAGTCTCAAAAGTGCAACTCTGTGC | 5408494 | 5415062 | 195 |
| GPF83 | GGAGTTTGCCTGCATCATCTCAAAAGCAGTG | 5427609 | 5431239 | 205 |
| GPF91 | GCACGGGAAAGTACCTGTAGTTACTAGGAAATG | 5445764 | 5451773 | 213 |
| GPF92 | GGGTACATGTGACTAGCATACACCTATTCAACC | 5451774 | 5453800 | 214 |

TABLE 2-continued

| PRIMER NAME | SEQUENCE (5'-3') | EcoR1 FRAGMENT POSITION START | END | FRAGMENT NAME |
|---|---|---|---|---|
| GPF93 | GGGGACTTCCTAATTCCACCTCTTTGGAGC | 5453301 | 5464851 | 215 |
| GPF95 | GTGTCTGTGACTTACTAAGGAGAAAGTCAATTCC | 5485402 | 5467640 | 217 |
| GPF96 | GTGCTAGAGATATGACTGGTACTTAATACAACTG | 5467641 | 5468314 | 218 |
| GPF97 | GCTGTTTCAATTTGTGCTGAGGGAGACTCTC | 5466315 | 5489998 | 219 |
| GPF100 | CAAGACCCTGTTCATGCTATTTCACAGCTCC | 5474899 | 5484552 | 222 |
| GPF101 | CCATTCAGACCCACATTCAGCTACTTCCTGT | 5484553 | 5485089 | 223 |
| GPF102 | GGGATATACAGTGGAGATGGCAGCAGCTGC | 5486060 | 5491878 | 224 |
| GPF103 | GATGAGTGAGGGTGATGCTAGGGCTTAGGATGC | 5491679 | 5506192 | 225 |
| GPF104 | CATAGGACACAACAGTGCCTGTAACACAG | 5506193 | 5510183 | 226 |
| GPF105 | CCTTCAGTGTTTGGCTCAATGTGGAACAAATCC | 5510164 | 5511056 | 227 |
| GPF106 | GTGGACAAGATGAGGTCAGTCATGGCCAGC | 5518465 | 5523217 | 230 |
| GPF111 | CCTAACATCTCACCTTTAGTAACTAGCAGAGCC | 5525106 | 5531048 | 233 |
| GPF115 | GGTGATTCATGAGCCTGGAACTGGTCCAACAG | 5532760 | 5535890 | 237 |
| 2. GENE DESERT REGION (ENr313) CHROMOSOME 16 | | | | |
| GD2 | AGCTTCACCTCTCAAACTACAGGACTGG | 60845578 | 60849115 | 2 |
| GD3 | GTATACTCAGTTGAGCAGCCCATGACAC | 60849116 | 60851238 | 3 |
| GD5 | GTTCTCTGTCTTATAATTATGCTACAAGAATGAGG | 60851792 | 60855935 | 5 |
| GD6 | GTTTAAGACCCTCAGTATACTAGTCATAGAAGG | 60855936 | 60856531 | 6 |
| GD7 | GATGCCATTTCTTATCTTGTCTTGGCAGGTC | 60858532 | 60888966 | 7 |
| GD8 | GCAGCAAAGCAAACCAAAAGAACAACAGG | 60868969 | 60873873 | 8 |
| GD9 | GTGTCATGGAATCAAAGGTGAGTGAGGG | 60873874 | 60878857 | 9 |
| GD10 | TATAAAGCTGCAAGGGAGGGTTGACTG | 60878858 | 60877889 | 10 |
| GD12 | CGAGATGATGCTAACCTCTATGAACCTC | 60880027 | 60880407 | 12 |
| GD17 | GGCTGGCTGAGGTCATTCATGCAATCTT | 60894707 | 60905483 | 17 |
| GD18 | CCATTCCATCATACACCCTCATCTCACTGCC | 60905484 | 60908417 | 18 |

Figure 12:
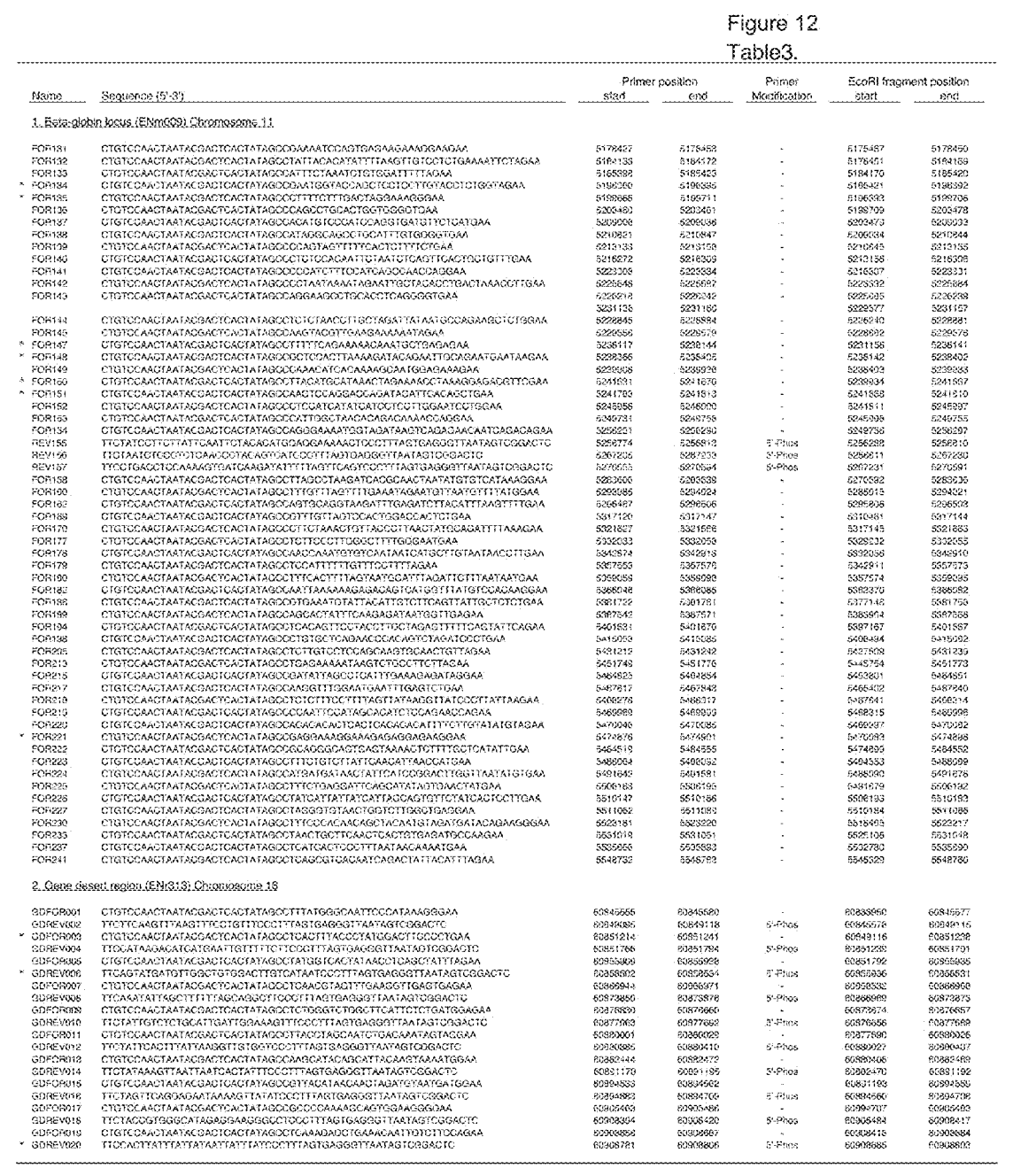

5C primer design. Forward and reverse primers corresponding to the 3' end of EcoRI restriction fragments. Primer homology lengths varied from 24 to 40 nucleotides and melting temperatures were centered at 72° C. The genomic uniqueness of all primers was verified with the SSAHA algorithm (Ning et al., *Genome Res.* 11: 1725-1729 (2001). Forward 5C primers were designed to include a 5'end tail that include (5'-3'): CTG followed by one Mme I restriction site (TCCAAC; SEQ ID NO:1), and a modified T7 Universal primer sequence (TAATACGACTCACTATAGCC; SEQ ID NO:2). Reverse 5C primers were designed to include a 3'end tail that include (5'-3'): a modified complementary T3 Universal sequence (TCCCTTTAGTGAGGGTTAATA; SEQ ID NO:3), one Mme I restriction site (GTCGGA; SEQ ID NO:4), followed by CTC. 5C forward and reverse primers each contained half of the EcoRI restriction site and only the reverse primers were phosphorylated at the 5' end. All 5C primers are presented in Table 3 (FIG. 12).

5C library preparation. 3C library (representing ~150,000 genome copies) or control library (5 ng) was mixed with salmon testis DNA (Sigma) to a total DNA mass of 1.5 μg, and with 1.7 fmol of each 5C primer in a final volume of 10 μl of annealing buffer (20 mM Tris-acetate pH 7.9, 50 mM potassium acetate, 10 mM magnesium acetate, and 1 mM DTT). Samples were denatured 5 min at 95° C. and annealed at 48° C. for 16 h. Annealed primers were ligated 1 h at 48° C. by adding 20 μl of ligation buffer (25 mM Tris-HCl pH 7.6, 31.25 mM potassium acetate, 12.5 mM magnesium acetate, 1.25 mM NAD, 12.5 mM DTT, 0.125% Triton X-100) containing 10 units of Taq DNA ligase (NEB). Reactions were terminated by incubating samples at 65° C. for 10 min. 5C ligation products were amplified by PCR using forward (T7 motif: CTGTCCAACTAATACGACTCACTATAGCC; SEQ ID NO:5) and reverse (T3 motif: GAGTCCGACTATTAAC-CCTCACTAAAGGGA; SEQ ID NO:6) primers. Six μl of ligation reaction was amplified with 10 pmol of each primer in 25 µl PCR reactions (32 cycles of 30 s denaturing at 95° C., 30 s annealing at 60° C., and 30 s extension at 72° C.). 5C libraries were purified with MinElute Reaction Cleanup Kit (Qiagen) to remove unincorporated primers and other contaminants as recommended by the manufacturer. Singleplex and 6-plex 5C analysis. 5C libraries from K562 and GM06990 (each representing ~150,000 genomes) or control libraries (5 ng) were incubated with individual 5C primer pairs and processed as described above, except that ligation reactions were amplified by 35 PCR cycles of 30 s denaturing at 95° C., 30 s annealing at 60° C., and 30 s extension at 72° C. Amplified 5C ligation products were resolved on 2% agarose gels and visualized with ethidium bromide (0.5 µg/ml). 6-plex 5C analysis was performed by mixing 6 distinct 5C primers with 3C or control libraries. Individual 5C ligation products of 6-plex samples were detected by PCR with specific internal PCR primers and, measured on agarose gels as described above. Linear range PCR detection of 5C products was verified by two-fold serial dilution titrations of multiplex samples.

Figure 9:
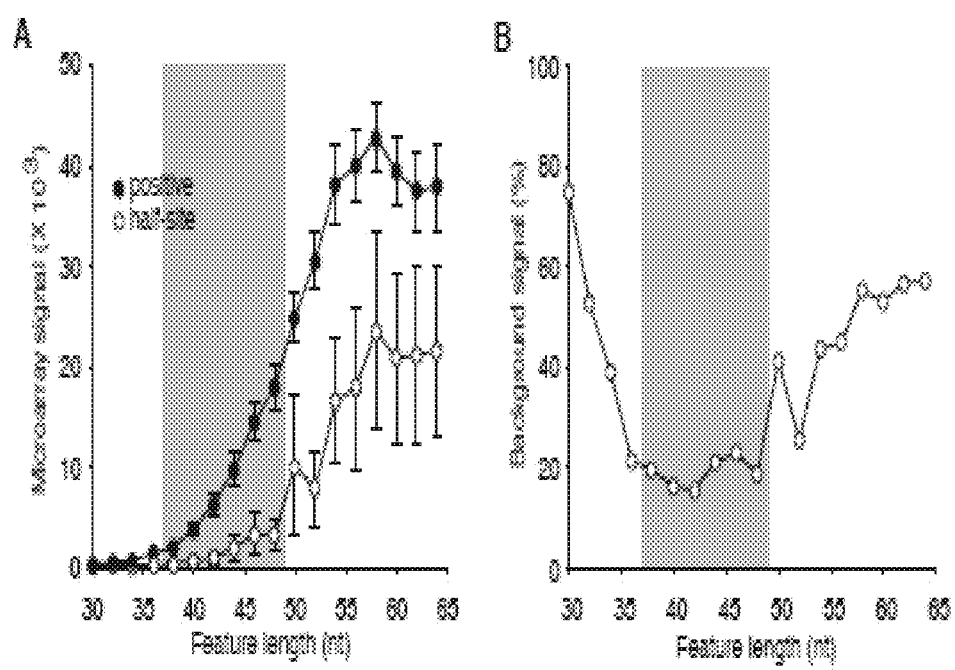
FIG. 9 shows that 5C array hybridization signals are optimal with features ranging from 38 to 48 nucleotides in length. (A) Raw intensity of positive and half-site background hybridization signals (y-axis) was determined for increasing probe lengths (x-axis). (B) Percentage of signal due to half-site hybridization for each probe length was estimated by calculating for each probe length the ratio of half-sites background signal and specific signal.

5C library microarray analysis. 5C libraries were prepared by performing multiplex LMA with 78 5C primers, and amplified with a 5'-Cy3-labelled reverse PCR primer complementary to the common 3' end tail sequence of reverse 5C primers (Cy3-T3 motif). Maskless array synthesis and hybridization were carried out with 100 ng of amplified 5C libraries at NimbleGen Systems Inc. (Madison, Wis.) as previously described (Kim et al., *Nature* 436:876-880 (2005); Nuwaysir et al., *Genome Res.* 12: 1749-1755 (2002); Selzer et al., *Genes Chromosomes Cancer* 44: 305-319 (2005); and Singh-Gasson et al., *Nat Biotechnol.* 17:974-978 (1999)). Each array featured the sense strand of predicted 5C ligation products. The arrays also contained inter-region negative controls that were used to identify problematic primers exhibiting high background signals due to half-site non-specific cross-hybridization. The arrays contained 18 replicates of increasing feature lengths ranging from 30 to 64 nucleotides, which were used to identify optimal array probe lengths (FIG. 9). Arrays were scanned using a GenePix4000B scanner (Axon Instruments, Molecular Devices Corp., Sunnyvale, Calif.) at 5-µm resolution. Data from scanned images were extracted using NimbleScan 2.0 extraction software (NimbleGen Systems, Inc.).

5C library high-throughput DNA sequencing analysis. 5C libraries were generated with 73 5C primers. Each library was amplified with 5'end phosphorylated PCR primers and processed for single molecule pyrosequencing as previously described (Margulies et al., *Nature* 437:376-380 (2005)). 550,189 sequence reads totaling million bases were obtained using the GS20 platform developed by 454 Life Sciences Corp. The mean read length was 108 bases (mode, 112 bases). Each read was blasted against all forward and reverse primers. For each sample, the number of reads that matched each of the 682 possible primer pairs (62 forward×1.1 reverse) was counted. These combinations include 159 possible interactions in the beta-globin locus, 72 interactions in the gene desert region, and 451 inter-region interactions. Data are summarized in Tables 4 and 5.

TABLE 4

|  | K582 (ON) | GM06990 (OFF) | CONTROL | TOTAL |
|---|---|---|---|---|
| A. COMPLETE DATASET |  |  |  |  |
| TOTAL | 197168 (100) | 183029 (100) | 195441 (100) | 555658 (100) |
| ASSIGNED | 185494 (94.1) | 152355 (93.4) | 178419 (91.3) | 516288 (92.9) |
| SINGLE PRIMER | 10382 (5.2) | 9480 (5.8) | 14378 (7.4) | 34200 (6.2) |
| UNCALLED | 1331 (0.7) | 1212 (0.8) | 2642 (1.3) | 5185 (0.9) |
| AMBIGUOUS | 1 (<0.01) | 2 (<0.01) | 2 (<0.01) | 5 (<0.01) |
| B. GENOMIC REGIONS |  |  |  |  |
| TOTAL | 63622 (32.3) | 32835 (20.1) | 146426 (74.4) | 241883 (43.5) |
| BETA-GLOBIN | 26098 (13.3) | 10453 (6.4) | 69791 (35.7) | 106340 (19.1) |
| GENE DESERT | 31180 (15.8) | 18507 (11.3) | 3832 (2.0) | 53519 (9.6) |
| BETA-GLOBIN/ GENE DESERT | 6346 (3.2) | 3875 (2.4) | 71803 (36.7) | 82024 (14.8) |
| B. GENOMIC REGIONS |  |  |  |  |
| TOTAL | 121872 (61.8) | 119520 (73.3) | 32993 (16.9) | 274385 (49.4) |
| BETA-GLOBIN | 75031 (38.0) | 76992 (47.2) | 17453 (8.9) | 189478 (30.5) |
| BETA-GLOBIN/ GENE DESERT | 46841 (23.8) | 42528 (26.1) | 15540 (8.0) | 104909 (15.9) |

Example II

3C Verification of Human Beta-Globin Locus Chromatin Loops

The presence of chromatin loops in the human beta-globin locus was first verified using the conventional 3C method. The locus was analyzed in the erythroleukemia cell line K562 and in the EBV-transformed lymphoblastoid cell line GM06990. K562 cells express high levels of epsilon and gamma-globin whereas GM06990 cells do not express the beta-globin locus (FIG. 11) 3C libraries were generated from both cell lines and a control library, which was generated using a series of minimally overlapping BAC clones. Interaction frequencies between the EcoRI fragment overlapping the HS5 element of the LCR and EcoRI restriction fragments throughout the beta-globin locus were determined by PCR. To allow direct quantitative comparison of interaction frequencies determined in K562 cells and GM06990 cells interaction frequencies were normalized using a set of 12 interaction frequencies detected in a control region, a conserved gene desert region on chromosome 16 (ENCODE region ENr313; (ENCODE-consortium 2004)).

The normalized results are presented in FIG. 2B. In both cell lines HS5 interacts frequently with adjacent DNA fragments. These interactions reflect non-functional random collisions resulting from the intrinsic close proximity of neighboring restriction fragments (Dekker, J., *Nat Methods* 3:17-21 (2006); and Dekker et al., *Science* 295:1306-1311 (2002)). The frequent random interactions between adjacent genomic fragments are likely dependent on local physical properties of the chromatin fiber and limit the ability to detect specific looping interactions between elements separated by small genomic distances (2-5 kb) (Dekker 2006, supra; Gheldof et al., 2006). Random collisions are predicted to decrease progressively for sites separated by increasingly large genomic distances. In K562 cells high interaction frequencies were observed specifically between the LCR and a restriction fragment located ~40 kb downstream and overlapping the A gamma-globin gene (HBG1), indicating the presence of a strong looping interaction. A frequent interaction between the LCR and the 3' HS1 element was also detected. This interaction was also present in GM06990 cells. Previous studies of the murine locus have shown that the analogous interaction also occurs in non-expressing erythroid precursor cells (Palstra et al., *Nat Genet* 35:190-194 (2003)). The analysis revealed less frequent random collisions between neighboring restriction fragments around the LCR in K562 cells as compared to GM06990 cells. Similar differences were observed in random collisions around the active and inactive FMR1 promoter. These differences may reflect transcription-dependent differences in chromatin expansion or changes in sub-nuclear localization.

Based on this analysis is was concluded that the conformation of the human betaglobin locus is comparable to the murine locus with looping interactions between the LCR and 3'HS1 in both expressing and non-expressing blood-derived cells. The interaction between the LCR and the active A gamma-globin gene is only observed in globin expressing K562 cells.

Example III

LMA Detection of 3C Ligation Products

Detection of chromatin loops in the beta-globin locus was used to develop and optimize the 5C technology. LMA was first performed with a single pair of 5C forward and reverse primers to verify that this method can quantitatively detect a ligation product in the context of a 3C library. A 5C primer pair was designed that recognizes a ligation product that is formed by two adjacent restriction fragments located in the gene desert control region. LMA was performed with this primer pair in the presence of increasing amounts of 3C library (generated from GM06990 cells) and the formation of ligated forward and reverse primers was quantified by PCR amplification with the pair of universal T7 and T3 primers. Ligation of 5C primers is not observed when non-specific DNA is present, is dependent on the amount of the 3C library and requires Taq ligase (FIGS. 2C and D). It was concluded that LMA can be used to quantitatively detect ligation products present in the 3C library.

Example IV

LMA Detection of LCR-A γ-Globin Gene Looping

Figure 7:
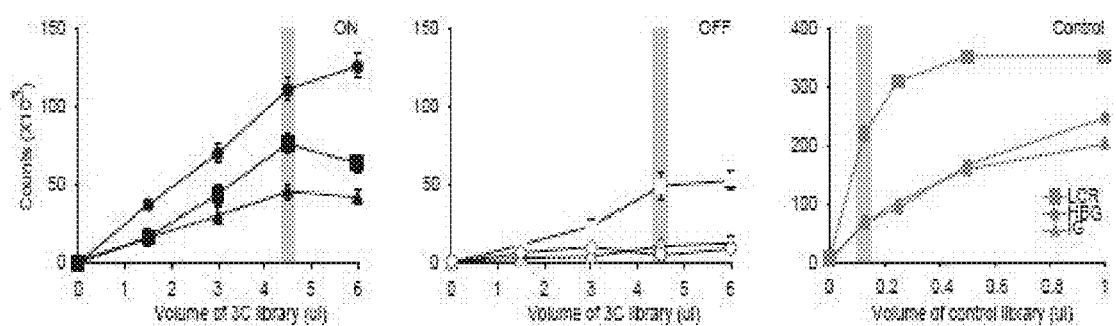
FIG. 7 shows singleplex LMA titration of 3C and control libraries with human beta-globin 5C primers.

This example describes the use of singleplex LMA to quantitatively detect chromatin looping interactions in the beta-globin locus. Interactions involving the LCR and three diagnostic fragments in the beta-globin locus (indicated as bars in FIG. 2A) were detected: a restriction fragment located just downstream of the LCR, a restriction fragment that overlaps the A gamma-globin gene HBG1 and a restriction fragment located in between the delta- and beta-globin genes. A reverse 5C primer was designed for the restriction fragment overlapping HS5 of the LCR and forward 5C primers for the three other fragments. The linear range of 5C detection was determined with individual pairs of 5C primers in the presence of increasing amounts of 3C libraries (from K562 and GM06990 cells) or control library (FIG. 7).

Interaction frequencies between HS5 and the three other sites in the beta-globin locus were determined by calculating the amount of ligated 5C primers obtained with the 3C library and the amount obtained with the control library. The interaction frequency between the two adjacent restriction fragments located in the gene desert control region was used for normalization. Normalized interaction frequencies are shown in FIG. 2E middle panel. The data obtained with LMA closely reproduced the 3C data, including the looping interaction between the LCR and the A gamma-globin gene. It was then tested whether the four interaction frequencies studied here (three in the beta-globin locus and one in the control region) can be detected and quantified in a single multiplex LMA reaction. LMA was performed with a mix of 6 5C primers and PCR with specific primers was used to quantify the frequency with which specific pairs of 5C primers were ligated. Normalized interaction frequencies were then calculated as described above. Similar results as with conventional 3C were obtained (FIG. 2E, right panel). Together, these experiments demonstrate that LMA can be used to quantitatively detect chromatin interactions.

Example V

5C Library Generation Using Multiplex LMA

Comprehensive 5C analysis of chromatin interactions throughout large genomic regions utilizes high levels of multiplexing in combination with a high-throughput method for analysis of 5C libraries. LMA was tested at higher levels of multiplexing. Two high-throughput detections methods were used to analyze 5C libraries: microarrays and quantitative DNA sequencing. 5C reverse primers were designed for each of the three EcoRI restriction fragments that overlap the LCR and 5C forward primers for 55 restriction fragments throughout a 400 kb region around the LCR. This primer design allows detection of looping interactions between each of the three sections of the LCR and the surrounding chromatin in parallel in a single experiment (see below). Ten 5C forward and 10 5C reverse primers were designed throughout a 100 kb region in the gene desert control region. Forward and reverse primers were designed to recognize alternating restriction fragments. This primer design scheme allows the detection of a matrix of interactions throughout the control region (see below).

Figure 8:
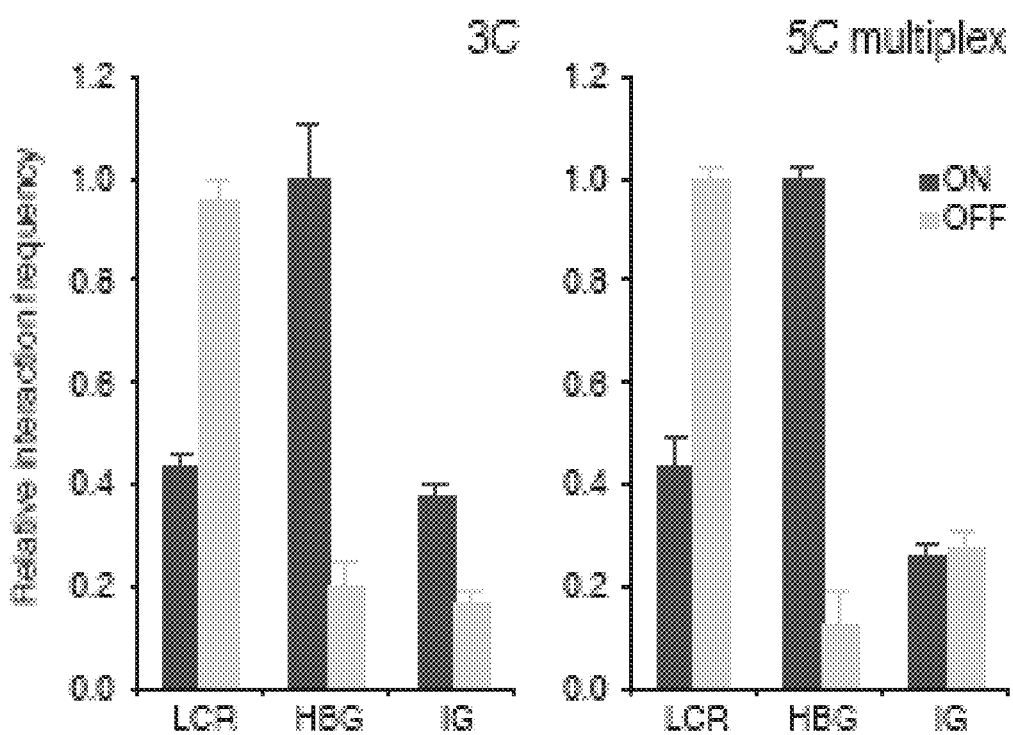
FIG. 8 shows quantitative detection of chromatin interactions using multiplex LMA with a mixture of 78 5C primers.

LMA was performed with a mixture of all 78 5C primers using 3C libraries from K562 and GM06990 and the control library as templates. Each 5C library contained up to 845 different 5C ligation products (the products of 13 reverse primers and 65 forward primers). These products included 165 possible interactions within the beta-globin locus, 100 interactions throughout the gene desert, and 590 interactions between the two genomic regions. It was verified that these 5C libraries represented quantitative copies of the selected fraction of the 3C libraries. To do this, the same set of four interaction frequencies as in FIG. 2E was analyzed using specific PCR primers to quantify the abundance of specific 5C ligation products in the 5C libraries and normalized interaction frequencies between the LCR and the three positions of the beta-globin locus were determined as described above. The 5C data closely reproduced the 3C interaction profile in both cell lines (FIG. 8) with strong looping interactions between the LCR and the A gamma-globin gene HBG1 in K562cells.

Example VI

5C Library Microarray Analysis

This example describes an analysis of microarray detection for comprehensive analysis of the composition of 5C libraries. First, to facilitate microarray detection we amplified the 5C libraries described above with Cy3-labeled universal primers. The labeled 5C libraries were then hybridized to a custom designed microarray that can detect specific 5C ligation products. Since each 5C product is composed of two half-sites, each corresponding to a 5C primer, cross-hybridization of non-specific 5C products can occur to probes that share one half-site. To assess half site cross-hybridization the microarray also contained probes that recognize only one of the 78 5C primers present in the library. To determine the optimal length of the microarray probes that allows the least cross-hybridization, each probe was spotted with 18 different lengths of half-sites ranging from 15 to 32 bases (total probe length ranging from 30 to 64 bases). 5C libraries were hybridized to the array and specific and half-site hybridization was quantified. It was found that probes that are composed of two half-sites with a length ranging from 19 to 24 bases displayed the lowest relative level of cross hybridization of half-sites (see FIG. 9). Data obtained with these six feature lengths was averaged and interaction frequencies were calculated by dividing the hybridization signal obtained with a 5C library by the signal obtained with the control library (see Table 7).

Example VII

5C Library Quantitative Sequencing Analysis

Figure 13:
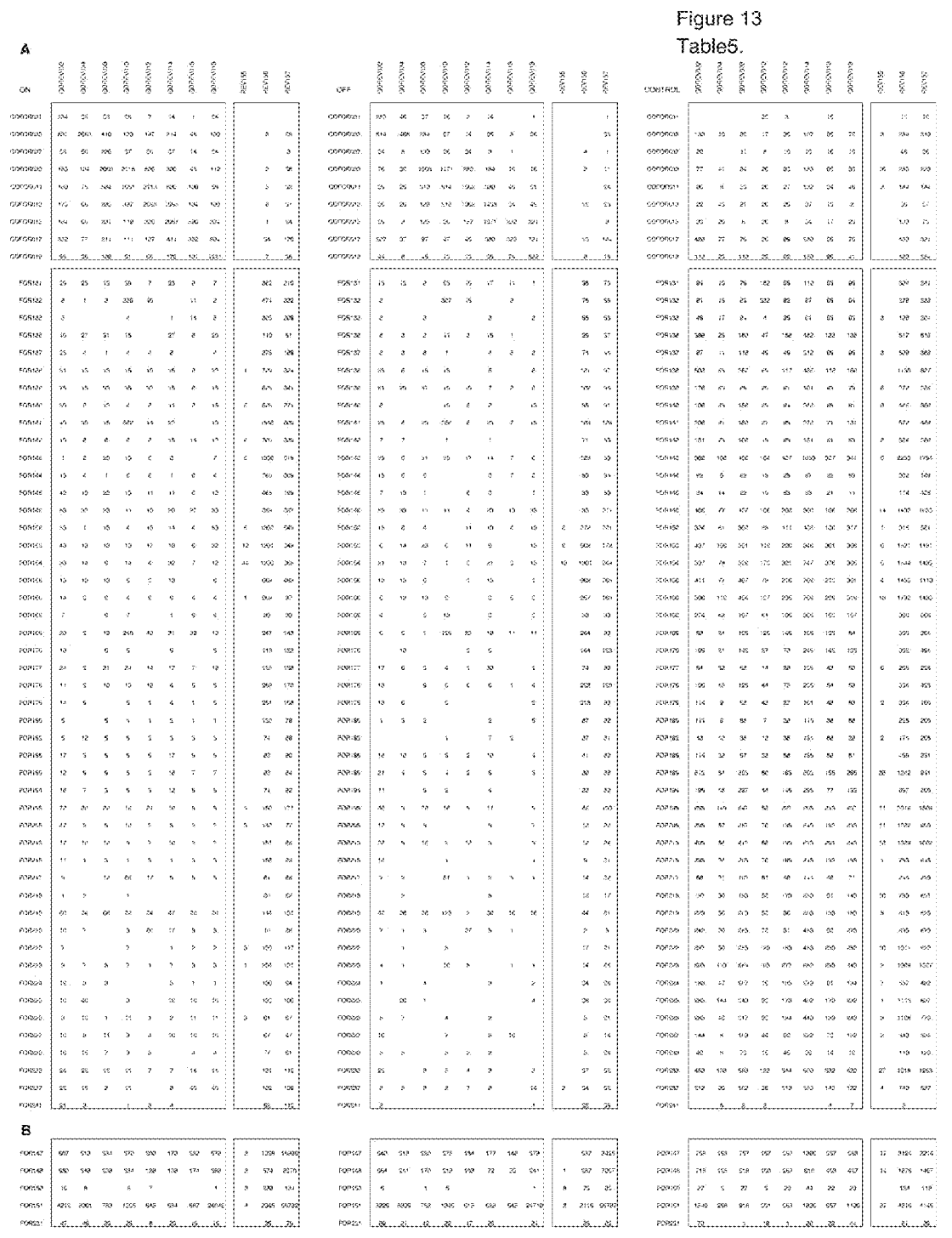
Figure 14:
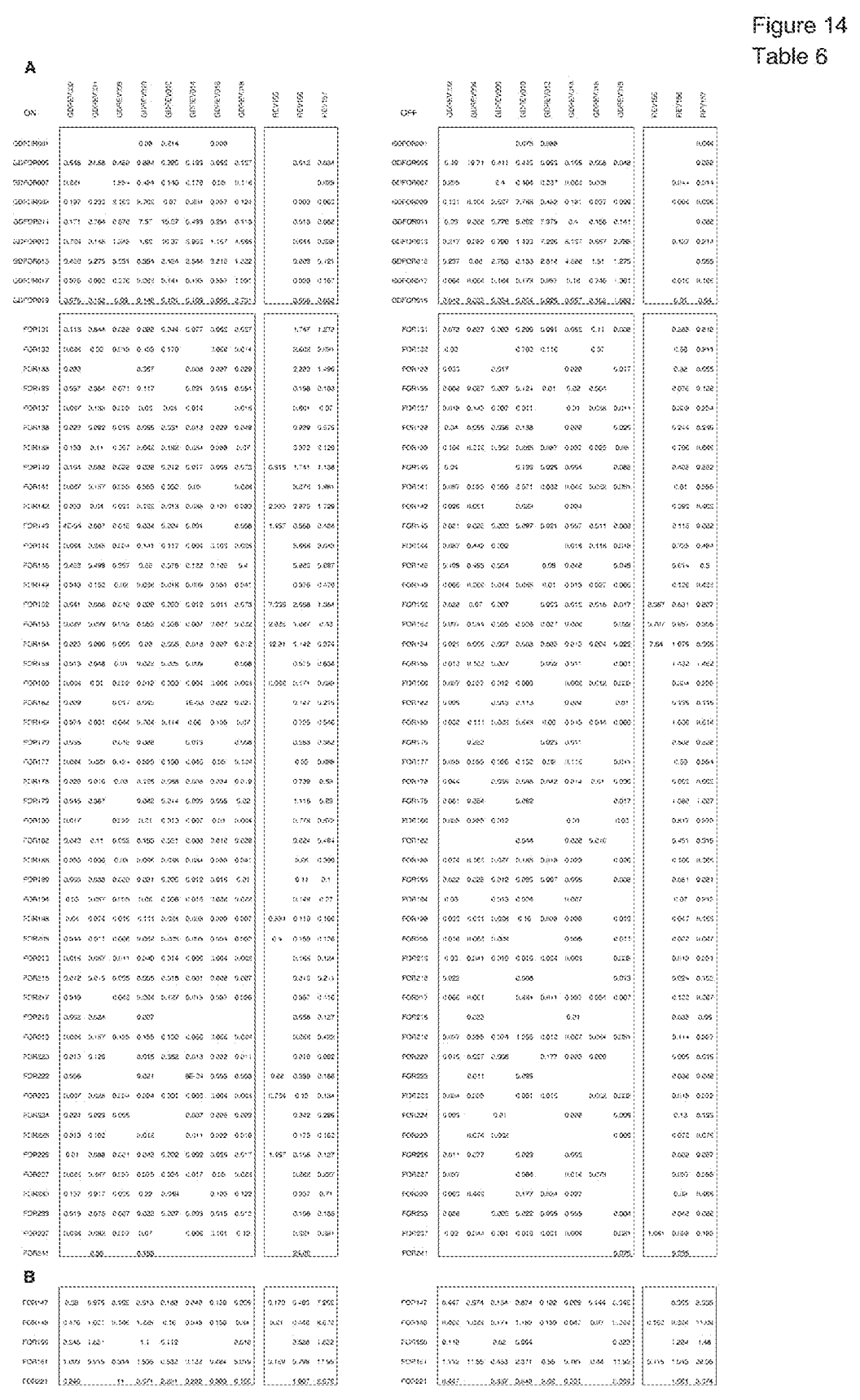

This example describes an analysis of the composition of 5C libraries by quantitative sequencing. 5C libraries are composed of linear DNA molecules that each are around 100 bp long, which makes them ideally suited for high-throughput single molecule pyrosequencing. Similar 5C libraries as used for microarray detection were generated, except that 5 of the 65 forward primers were left out. 5C and control libraries were analyzed using the GS20 platform developed by 454 Life Sciences Corp (Margulies et al., *Nature* 437:376-380 (2005). For each library at least 160,000 sequence reads were obtained (Table 4). For each sequence it was determined which pair of ligated 5C primers it represented and the number of times each specific 5C ligation product was sequenced was counted (see Table 5 (FIG. 13)). As each ligation product was sequenced many times (median count for intra-chromosomal interactions was 133 for K562, 53 for GM06990 and 134 for the control library) a quantitative determination of interaction frequencies was obtained. Interaction frequencies were calculated by dividing the number of times a 5C product was sequenced in a 5C library by the number of times it was sequenced in the control library (Table 6 (FIG. 14)).

Example VIII

Large-Scale 5C Analysis Of the β-Globin Locus

This example describes the analysis of the interaction profiles of HS5 throughout the 100 kb betaglobin locus as detected on the microarray (FIG. 3A) and by quantitative sequencing (FIG. 3C). For comparison, the same interaction profile was also determined by conventional 3C and data was normalized using interaction frequencies determined within the control region (FIG. 3B). Both microarray detection and quantitative sequencing reproduced the overall 3C interaction profile of the beta-globin locus in K562 and GM06990 cells. In all three datasets it was found that the LCR specifically and strongly interacted with the gamma-globin genes in K562 cells. In both cell lines the looping interaction between the LCR and the 3' HS1 element was detected. 3C and 5C analyses also revealed strong interactions between the LCR and a region located between the gamma- and delta-globin genes in K562 cells. This region contains the beta-globin pseudogene, which is weakly expressed in K562 cells, but is silent in GM06990, and the initiation site for an intergenic transcript (Gribnau et al., *Mol Cell.* 5:377-386 (2000)).

Figure 11:
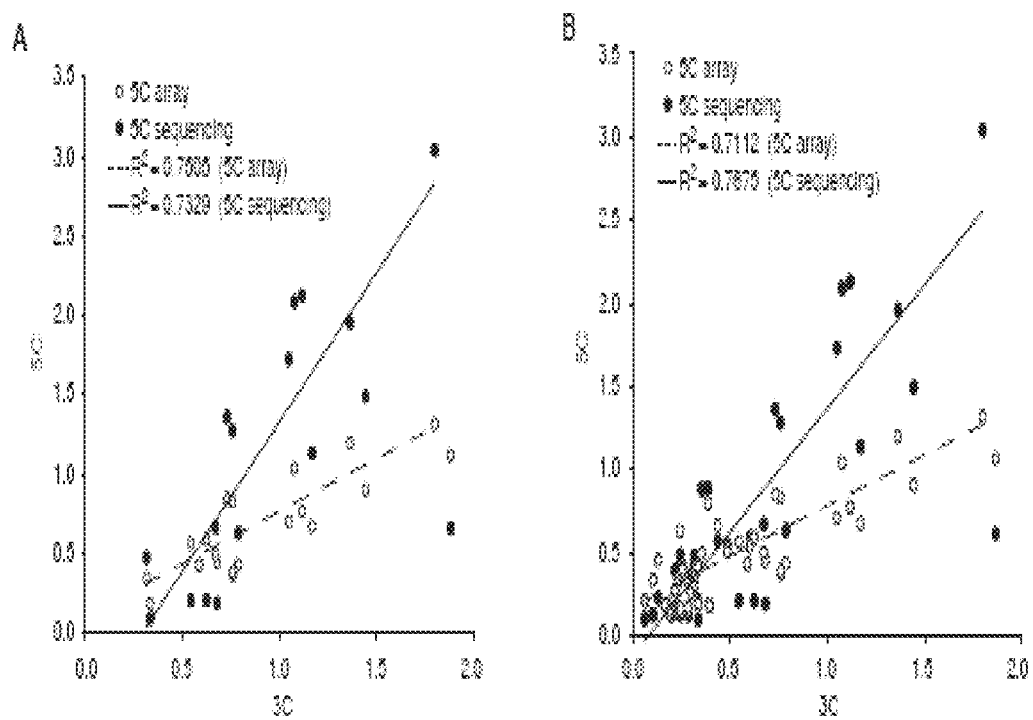
FIG. 11 shows a scatter plot analysis of 5C and 3C results from the human beta-globin profiles in K562 cells. (A) Correlation between 5C and 3C data shown in FIG. 3. (B) Correlation between 5C and 3C data shown in FIG. 4.

The 5C and 3C datasets were compared directly by calculating for each pair of interacting fragments the fold difference between their interaction frequencies as determined by 5C and 3C. The difference in 5C data obtained by microarray detection and conventional 3C is generally less than 2-fold (FIG. 3D). Larger differences were observed when 5C data obtained by quantitative sequencing was compared to 3C data (FIG. 3D). The present invention is not limited to a particular mechanism. Indeed, an understanding of the mechanism is not necessary to practice the present invention. Nonetheless, it is contemplated that this may be due to the fact that the dynamic range of quantitative sequencing is higher than that of semiquantitative PCR or microarrays, which results in higher peaks and lower valleys in the profile obtained by sequencing as compared to semi-quantitative PCR. The correlation between 5C and 3C data was determined directly by plotting the data in a scatter plot (FIG. 11). A high degree of correlation ($r2=0.73$) was found for the dataset obtained by sequencing as well as for the dataset obtained on the microarray ($r2=0.75$)).

Taken together, these results show that 5C in conjunction with microarray detection or quantitative sequencing is a powerful methodology to quantitatively detect chromatin interactions in a high-throughput setting.

Example IX

Interactions Between HS5 and Upstream Elements

In the mouse the LCR interacts with HS elements (HS-62.5/HS-60) located up to 40 kb upstream of the LCR (Palstra et al., *Nat Genet* 35:190-194 (2003); Tolhuis et al., *Locus. Mol Cell* 10:1453-1465 (2002)). It is not known if functionally equivalent elements are present in this region of the human genome. It has been noted that olfactory receptor genes located approximately 90 kb upstream of the LCR are orthologous to ones located 40 kb upstream of the murine locus (Bulger et al. 2000), indicating that these regions are related. In addition, the murine HS-62.5/HS-60 element is embedded in a sequence that is similar to a sequence located ~90 kb upstream of the human LCR (Bulger et al. 2003). These observations indicate that the region located ~90 kb upstream of the human LCR is orthologous to the region located ~40 kb upstream of the murine locus suggesting that this region may also interact with the LCR in human cells. To assess in an unbiased fashion whether the LCR interacts with any upstream elements in the human locus the 5C experiment described above was designed to include analysis of a large region located upstream of the LCR. The interaction profiles obtained by microarray detection and quantitative sequencing of HS5 with a region up to 280 kb upstream of the LCR were analyzed. Both datasets showed that interactions throughout this region are generally much lower than those observed between the LCR and the beta-globin locus. In both cell lines elevated interaction frequencies were detected throughout a large domain located 50 to 100 kb upstream of the LCR (FIG. 4A). This result was confirmed by conventional 3C (FIG. 4A, compare top, middle and bottom panels). This region contains three olfactory receptor genes and multiple HS sites (Bulger et al., Mol Cell Biol. 23: 5234-5244 (2003)).

The present invention is not limited to a particular mechanism. Indeed, an understanding of the mechanism is not necessary to practice the present invention. Nonetheless, it is contemplated that these results suggest that the region located 50-100 kb upstream of the LCR in the human genome is in relative close proximity of the LCR and therefore is functionally equivalent to the genomic region located 40 kb upstream of the LCR in the murine locus. In addition, these results illustrate that large-scale mapping of interactions using 5C can greatly facilitate the discovery of the locations of novel putative regulatory elements.

Example X

Parallel Analysis of Multiple Interaction Profiles

Figure 15:
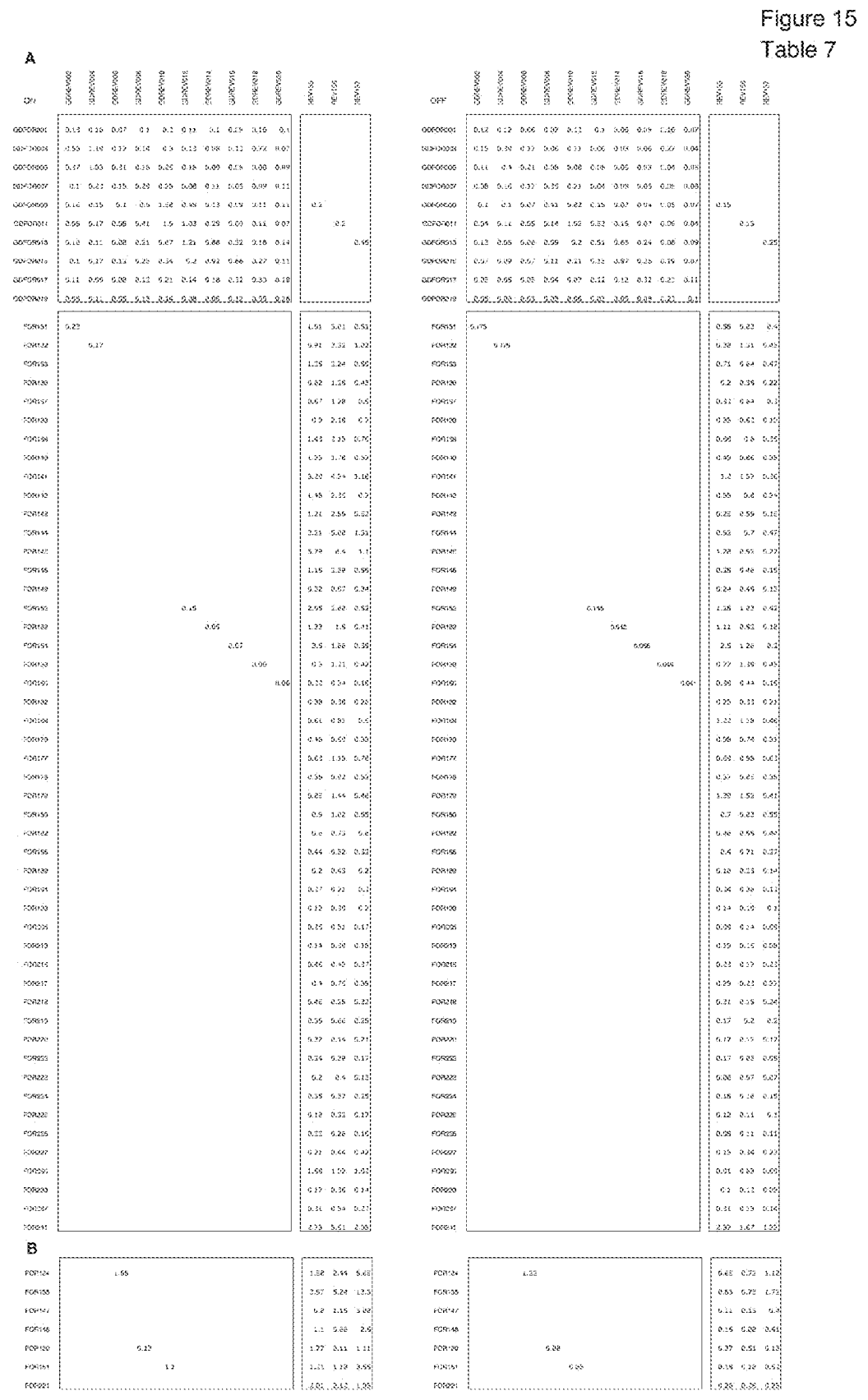

A major advantage of 5C is the fact that interactions between multiple elements of interest and other genomic elements can be analyzed in parallel in a single experiment. The 5C experiment described here was designed to illustrate this aspect of the methodology. As described above 5C forward and reverse primers were designed to allow simultaneous detection of interaction profiles of each of the three sub-sections of the LCR with the 400 kb surrounding chromatin. Data obtained by microarray analysis and quantitative sequencing of 5C libraries showed that the interaction profile of the restriction fragment overlapping HS2/3/4 of the LCR fragment is very similar to that of HS5 (FIG. 4C). In K562 cells HS2/3/4 interacted more frequently with sites throughout the beta-globin locus than HS5, suggesting that these HSs may contribute most to the formation of the chromatin loops with LCR. 5C analysis of the LCR 3' end, which contains HS1, did not yield sufficient levels of ligation products to obtain significant number of sequence reads. Analysis of microarray hybridization signals confirmed the low levels of ligation products formed with the 5C primer for HS1, but the general patterns of interaction frequencies for K452 and GM06990 cells were consistent with the patterns obtained for HS5 and HS2/3/4 (Table 7 (FIG. 15)).

Example XI

Large-Scale 5C Analysis of the Gene Desert Control Region

Figure 5:
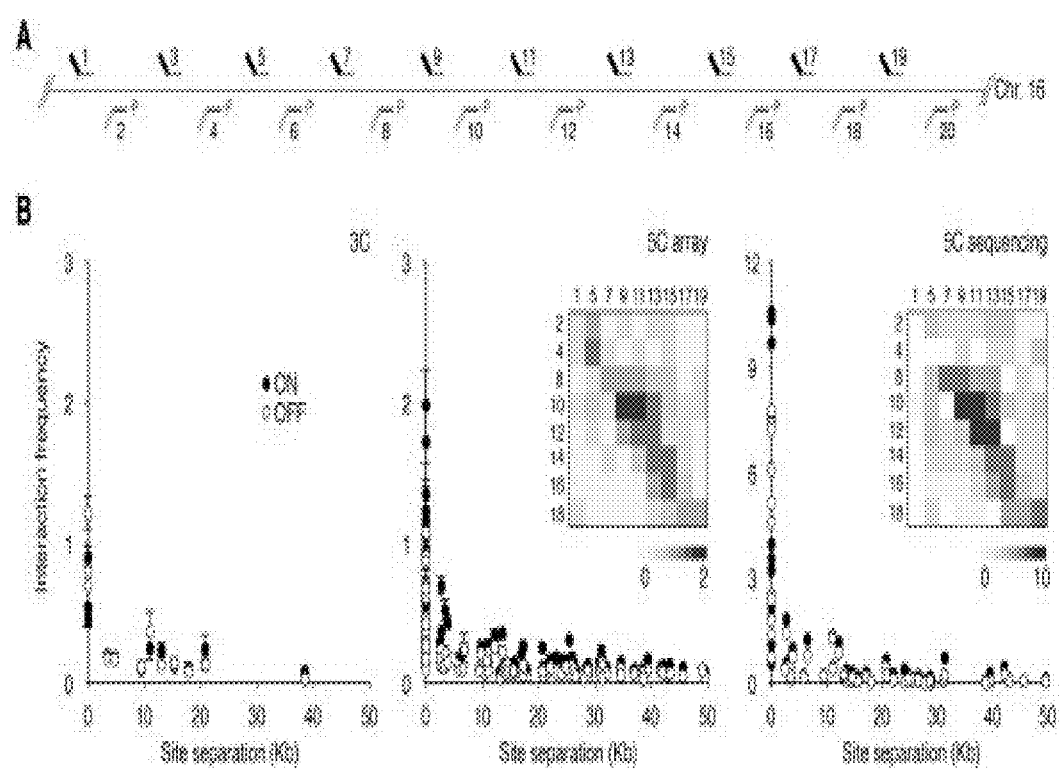
FIG. 5 shows an analysis of the conformation of the gene desert control region. (A) Positions of alternating 5C forward (top) and reverse (bottom) primers throughout the gene desert control region. (B) Chromatin interaction frequencies of the gene desert region as determined by conventional 3C (left panel), by 5C and microarrays (middle) and by 5C and quantitative sequencing (right panel).
Figure 6:
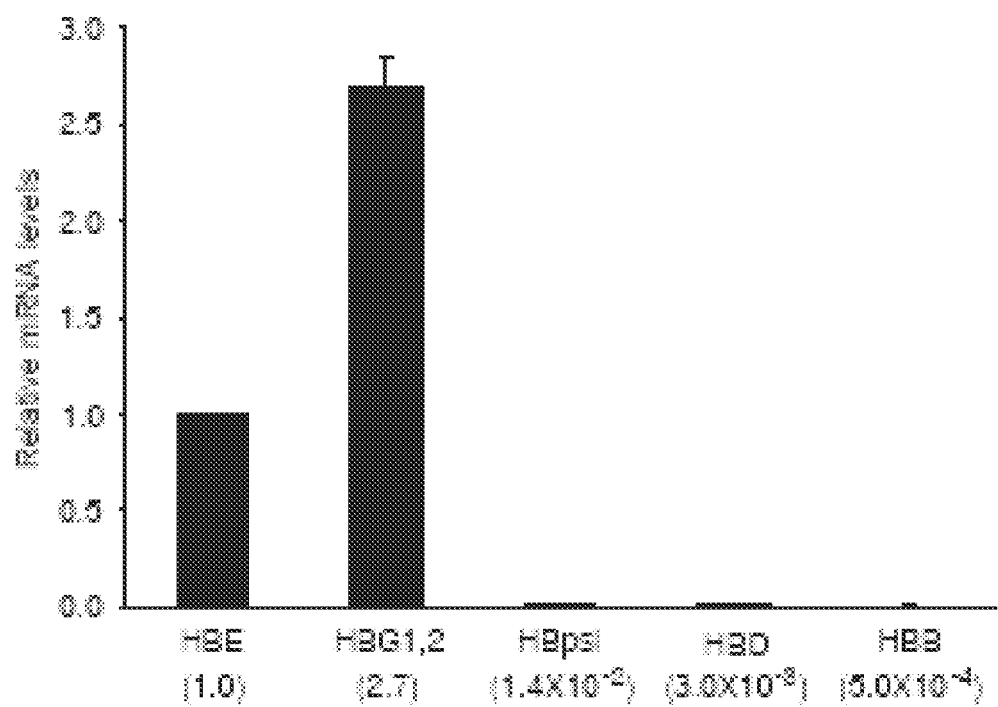
FIG. 6 shows relative beta-globin mRNA levels in K562 cells.

The 5C analysis of the beta-globin locus was focused at the mapping of interactions between a fixed regulatory element, the LCR, and the surrounding chromatin. 5C experiments can also be designed so that a more global dataset is obtained, which is particularly useful when the positions of regulatory elements are poorly defined. This example provides an example of an alternative 5C primer design scheme that provides insights into the general spatial conformation of a genomic region. The 5C analysis described above included 10 forward and 10 reverse 5C primers for restriction fragments located in the gene desert control region (FIG. 5A). Forward and reverse primers were designed for alternating restriction fragments (FIG. 5A). Combined these primers detected chromatin interactions throughout the region. Interaction frequencies determined by microarray analysis and quantitative sequencing were plotted against the genomic distance between the interacting restriction fragments. In both cell lines, interaction frequencies were found to decrease with increasing genomic distance (FIG. 5B). Similar results were obtained by conventional 3C analysis. The graphs in FIG. 5 do not reveal where along the chromosome particular interaction frequencies were measured. To better illustrate that a global interaction map is obtained, interaction frequencies between forward and reverse 5C primers as two-dimensional heatmaps in which the color of each square is an indication of the interaction frequency between restriction fragments were generated. Interaction frequencies displayed along the diagonal reflect interactions between fragments located close together along the chromosome. The overall pattern of interactions observed in this gene desert region is very different from that observed in the beta-globin locus and is consistent with an overall linear conformation of the chromatin fiber (Dekker, (2006), supra; Dekker et al., (2002), supra; and Rippe, Trends Biochem Sci 26:733-740 (2001).

Example XII

Chromatin Immunoprecipitation

Chromatin immunoprecipitation (ChIP) assays were performed essentially as described in Gombert et al., (Mol Cell Biol. 23: 9338-9348 (2003)) with minor modifications. Chromatin from exponentially growing K562 cells (8×107 total) was crosslinked in 1% formaldehyde for 3 minutes at room temperature. After addition of glycin to a final concentration of 0.125M, cells were washed and sonicated with 10 cycles (30 sec each) in an ethanolice bath. The average size of DNA in the cross-linked chromatin was approximately 200 to 500 bp. Chromatin from the equivalent of $1 \times 10^7$ cells was incubated with polyclonal antibodies to CTCF (purchased from Upstate Biotechnology) for 4 hours. DNA from immunoprecipitated and washed chromatin was recovered as described in (Gombert et al. 2003, supra), and subjected to PCR with primers listed in Table 8.

Results are shown in FIG. 10. Analysis of CTCF binding to sites within the gamma-delta intergenic region (g/d1, g/d2) and the LCR (5'HS5) of the beta-globin gene locus in K562 cells. (A) Result of a representative quantitative duplex PCR with DNA recovered from a ChIP with antibodies to CTCF. DNA from input chromatin (Input) and immunoprecipitated chromatin (CTCF-ChIP) was PCR-amplified with primers specific for the human myotonic dystrophy gene (DM1), the LCR (5'HS2), or the gamma-delta intergenic region (g/d1 and g/d2) of the beta-globin gene locus. Quantitative PCR reactions also contained a reference primer set specific for the promoter-region of the beta-globin gene (beta-ref) for normalization. (B) Quantitative results of two independent replicate ChIP experiments. Normalized signals (Y-axis) represent the ratio of signals obtained by experimental primer sets (DM1, g/d1, g/d2, 5'HS5) and reference primer set (beta-ref).

TABLE 8

| PRIMER NAME | SEQUENCE [5'-3'] | TPCR AMPLICON SIZE (bp) |
|---|---|---|
| DM1 FORWARD | CAGTTCACAACCGCTCCGAG | 142 |
| DM1 REVERSE | GCAGCATTCCCGGCTACAAG | |
| g/c1 FORWARD | GGAGATCAGCACCTTCTTGC | 130 |

TABLE 8-continued

| PRIMER NAME | SEQUENCE [5'-3'] | TPCR AMPLICON SIZE (bp) |
|---|---|---|
| g/c1 REVERSE | ATCCCACAGTCTCCTGGTTG | |
| g/c2 FORWARD | GTCAAGGGTGGGTTGTGACT | 154 |
| g/c2 REVERSE | GAAAATGGAGGGGAAGGAGG | |
| 5HS5 FORWARD | TCCAGATGTCCTGTCCCTGT | 148 |
| 5HS5 REVERSE | GCTGAAGCTGCTGTTATGACC | |

All publications and patents mentioned in the above specification are herein incorporated by reference. Various modifications and variations of the described method and system of the invention will be apparent to those skilled in the art without departing from the scope and spirit of the invention. Although the invention has been described in connection with the specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The invention claimed is:

1. A method, comprising:
   a) providing a chromosome conformation capture (3C) library constructed from cross-linked interacting chromatin segments derived from at least one cell, wherein said 3C library comprises a plurality of ligation products representative of interacting genomic loci, wherein each of said plurality of ligation products is formed by two adjacent restriction fragments;
   b) annealing unique primer pairs to said plurality of ligation products; and
   c) ligating said annealed unique primer pairs together, thereby providing a carbon copy chromosome capture (5C) library.

2. The method of claim 1, wherein said plurality of unique primer pairs comprises at least 10 unique primer pairs.

3. The method of claim 1, wherein said plurality of unique primer pairs comprises at least 100 unique primer pairs.

4. The method of claim 1, wherein said plurality of unique primer pairs comprises at least 500 unique primer pairs.

5. The method of claim 1, wherein said plurality of unique primers pairs comprises at least 1000 unique primer pairs.

6. The method of claim 1, wherein said plurality of unique primers pairs comprises at least 10,000 unique primer pairs.

7. The method of claim 1, wherein said plurality of unique primers pairs comprises at least 100,000 unique primer pairs.

8. The method of claim 1, wherein said ligation products comprise nucleic acids approximately 100 bps in length.

9. The method of claim 1, wherein said 5C library is representative of long-range genomic interactions.

10. The method of claim 9, wherein said long-range genomic interactions comprise interaction of activators or repressors of gene expression with a gene.

11. The method of claim 9, wherein said long-range genomic interactions comprise interaction of chromatin on different chromosomes.

12. The method of claim 1, wherein said at least one cell is an animal cell.

13. The method of claim 1, wherein said at least one cell is selected from the group consisting of a bacterial cell, and a plant cell.

14. The method of claim 9, further comprising the step of calculating interaction frequencies for said long range genomic interactions.

15. The method of claim 1, wherein said 3C library has one or more variant genes selected from at least one of the group consisting of polymorphisms, genomic deletions, genomic fusions, genomic translocations, and genomic inversions.

16. The method of claim 1, further comprising step (d) amplifying said 5C library with a single pair of universal primers.

17. The method of claim 16, further comprising step (e) analyzing said amplified 5C library with a high-throughput application.

18. A method, comprising:
   a) providing a chromosome conformation capture (3C) library constructed from cross-linked interacting chromatin segments derived from at least one cell, wherein said 3C library comprises a plurality of ligated nucleic acid restriction fragments with a junction representative of interacting genomic loci; and
   b) performing multiplex ligation mediated amplification with primer pairs targeting said junction.

19. The method of claim 18, wherein said primer pairs are selected from the group consisting of at least 10 unique primer pairs, at least 100 unique primer pairs, at least 500 unique primer pairs, at least 1000 unique primer pairs, at least 10,000 unique primer pairs, and at least 100,000 unique primer pairs.

20. The method of claim 18, wherein said ligated restriction fragments comprise nucleic acids approximately 100 bps in length.

21. The method of claim 18, wherein said multiplex ligation mediated amplification creates a 5C library.

22. The method of claim 21, wherein said 5C library is amplified with a single pair of universal primers.

23. The method of claim 22, wherein said amplified 5C library is analyzed with a high-throughput application.

24. The method of claim 23, wherein said high throughput application comprises sequencing.

25. The method of claim 23, wherein said high throughput application is performed using a microarray.

26. The method of claim 21, wherein said 5C library is representative of long-range genomic interactions.

27. The method of claim 26, wherein said long-range genomic interactions comprise interaction of activators or repressors of gene expression with a gene.

28. The method of claim 26, wherein said long-range genomic interactions comprise interaction of chromatin on different chromosomes.

29. The method of claim 18, wherein said at least one cell is an animal cell.

30. The method of claim 18, wherein said at least one cell is selected from the group consisting of a bacterial cell, and a plant cell.

31. The method of claim 26, further comprising the step of calculating interaction frequencies for said long range genomic interactions.

32. The method of claim 18, wherein said 3C library has one or more variant genes selected from at least one of the group consisting of polymorphisms, genomic deletions, genomic fusions, genomic translocations, and genomic inversions.

33. The method of claim 17, wherein said high throughput application comprises sequencing.

34. The method of claim 17, wherein said high throughput application is performed using a microarray.

* * * * *